Figure 2A:
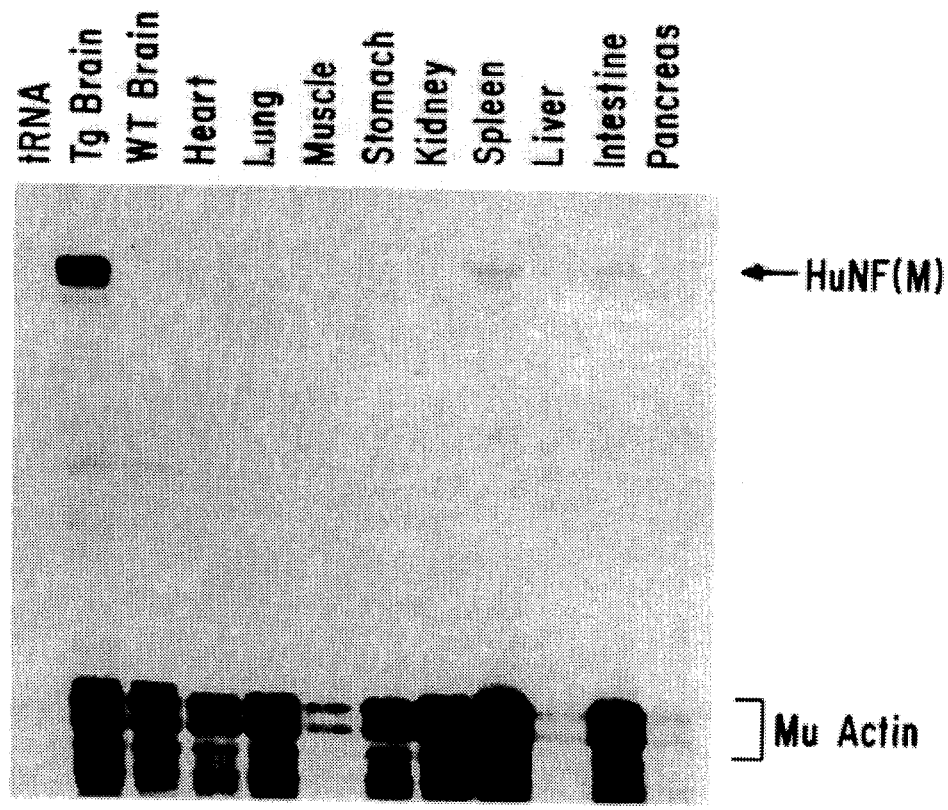

United States Patent [19]

Lazzarini

[11] Patent Number: 5,602,299

[45] Date of Patent: Feb. 11, 1997

[54] TRANSGENIC ANIMAL MODELS FOR NEURODEGENERATIVE DISEASE

[75] Inventor: Robert A. Lazzarini, New York, N.Y.

[73] Assignee: Mount Sinai School of Medicine of the City University of New York, New York, N.Y.

[21] Appl. No.: 950,092

[22] Filed: Sep. 23, 1992

[51] Int. Cl.$^6$ .......................... A01K 67/00; C12N 15/00
[52] U.S. Cl. .................. 800/2; 800/DIG. 1; 435/172.3; 435/320.1; 536/23.5
[58] Field of Search ............................ 800/2; 435/172.1, 435/172.3, 173; 935/6, 9; 536/23.1, 23.5, 24.1; 424/9

[56] References Cited

PUBLICATIONS

Geisler, N. and Weber, K., 1981, J. Mol. Biol. 151: 565–571.
Sharp, G. A. et al., 1982, Exp. Cell Res. 137:403–413.
Liem, R. K. H. and Hutchinson, S. B., 1982, Biochemistry 21:3221–3226.
Julien, J.-P. and Mushynski, W. E., 1983, J. Biol. Chem. 258:4019–4025.
Portier, M. M. et al., 1984, Dev. Neurosci. 6:335–344.
Pachter, J. S. and Leim, R. K. H., 1984, Dev. Biol. 103:200–210.
Hirokawa, N. M. et al., 1984, J. Cell Biol. 98:1523–1536.
Hoffman, P. N., et al., 1984, J. Cell Biol. 99:705–714.
Bennett, G. S. and DiLullo, C., 1985, Dev. Biol. 107:107–127.
Pierre, M. et al., 1985, Ann. N.Y. Acad. Sci. 495:808–811.
Carden, M. J. et al., 1985, J. Biol. Chem. 260:9805–9817.
Lee, V. M.-Y. et al., 1986, J. Neurosci. 6:2179–2186.
Levy, E. et al., 1987, Eur. J. Biochem. 166:71–77.
Kang, J. et al., 1987, Nature 325:733–736.
Kollias, G. et al., 1987, Proc. Natl. Acad. Sci. USA 84:1492–1496.
Julien, J.-P. et al., 1987, Biochem. Biophys. Acta 909:10–20.
Julien, J.-P., et al., 1987, Genes and Dev. 1:1085–1095.
Myers, M. W. et al., 1987, EMBO J. 6:1617–1626.
Gordon, J. et al., 1987, Cell 50:445–452.
Lee, V. M.-Y. et al., 1987, J. Neurosci. 7:3474–3488.
Leonard, D. G. B. et al., 1988, J. Cell Biol. 106:181–193.
Lee, V.-M. Y. et al., 1988, Proc. Natl. Acad. Sci. USA 85:1998–2002.
Lees, J. F. et al., 1988, EMBO J. 7:1947–1955.
Steinert, P. M. and Roop, D. R., 1988, Ann. Rev. Biochem. 57:593–625.
Hisanaga, S.-I. and Hirokawa, N., 1988, J. Mol. Biol. 202:297–305.
Julien J.-P. et al., 1988, Gene 68:307–314.
Wible, B. A. et al., 1989, Proc. Natl. Acad. Sci. USA 86:720–724.
Pleasure, S. J. et al., 1989, J. Neurosci. 9:698–709.
Szaro, B. G. et al., 1989, Dev. Brain Res. 48:87–103.
Hyman, B. T. et al., 1989, Neurosci. Lett. 101:352–355.
Evans, D. A. et al., 1989, JAMA 262:2551–2556.
Lendahl, U. L. et al. 1990, Cell 60:585–595.
Fliegner, K. H. et al., 1990, EMBO J. 9:749–755.
Vidal, M. et al., 1990, EMBO J. 9:833–840.
Pleasure, S. J. et al., 1990, J. Neurosci. 10:2428–2437.
Forss–Petter, S. et al., 1990, Neuron 5:187–197.
Montiero, M. J., 1990, J. Cell Biol. 111:1543–1557.
Shaw, C., 1991, Neurofilament Proteins, In "The Neuronal Cytoskeleton", Burgoyne, R. R., ed., pp. 185–214, Wiley–Liss, Inc., N.Y.
Balin, B. J. et al., 1991, Brain Res. 556:181–195.

(List continued on next page.)

*Primary Examiner*—Jacqueline M. Stone
*Assistant Examiner*—Bruce Campbell
*Attorney, Agent, or Firm*—Pennie & Edmonds

[57] ABSTRACT

The design, construction, and use of transgenic animals which exhibit features, including neurofibrillary tangles and aluminum sensitivity, is described. The founder transgenic animals of the invention are produced by methods well known in the art, and utilize DNA sequences designed to express all or any part of the human neurofilament subunit genes, NF-L, NF-M, NF-H, in a neural-enriched manner.

3 Claims, 19 Drawing Sheets

OTHER PUBLICATIONS

Tohyama, T. et al., 1991, J. Comp. Neurol. 310:285–299.
Katsman, R. and Saitoh, T., 1991, FASEB J. 5:278–286.
Quon, D. et al., 1991, Nature 352:239–241.
Marx, J., 1991, Science 253:266–267.
Wirak et al., 1991, Science, 253:323–325.
Wong, P. C. et al., 1991, (Abstract) J. Cell Biol. 115:122a.
Xu, Z.–S. et al., 1991, (Abstract) J. Cell Biol. 115:163a.
Cote, F. et al., 1991, (Abstract) J. Cell Biol. 115:163a.
Kawabata, S. et al., 1991, Nature 354:476–478.
Kawabata, S. et al., 1991, Nature 356:23.
Kawabata, S. et al., 1991, Nature 356:265.
Brady, S. T., 1993, Cell 73:1–3.
Xu, Z. et al., 1993, Cell 73:23–33.
G Friedrich et al (1991) Genes Dev. 5:1513–1523 (Abstract only).
M R Capecchi (1989) Science 244:1288–1292.
E Robertson et al (1986) Nature 323: 445–448.
V M Y Lee et al (1992) Mol Brain Res 15:76–84 (Abstract only).
M B Gagne et al (1991) Molecular Reproduction and Development 29:6–15.

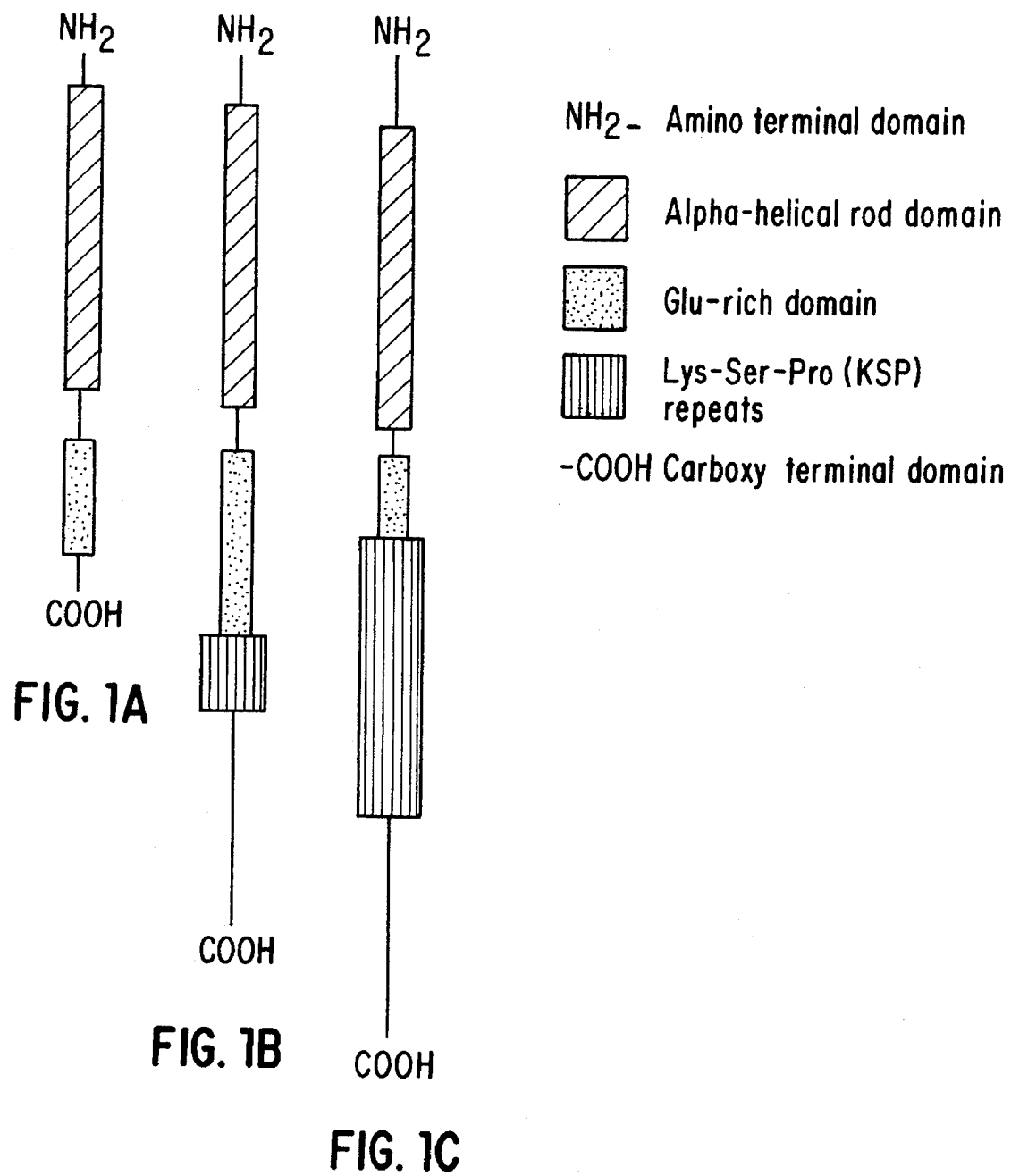

ALUMINUM TREATMENT OF 3 MONTHS OLD NF(M)27 AND WILD TYPE MICE

| Mouse # | Tangles | Pick-like Bodies | Ranking | Code |
|---|---|---|---|---|
| 24 | 2 | 2 | 1 | wt |
| 25 | 24 | 50 | 5 | NF27 |
| 26 | 3 (only 1 good one) | 9 (all good) | 3 | NF27 |
| 27 | 32 | 17 | 6 | NF27 |
| 28 | 12 | 26 | 4 | NF27 |
| 29 | 0 | 2-4 (all very questionable) | 2 | wt |

FIG. 13

ND NEURODEGENERATIVE DISEASE

1. INTRODUCTION

The present invention relates to the production and use of transgenic animal models for human neurodegenerative disorders including, but not limited to Alzheimer's disease. In addition, the transgenic animals provide models for neurological changes that occur during the normal course of human aging. DNA sequences that drive neuron-enriched expression of the human midsized neurofilament subunits in transgenic animals are described. As demonstrated by the working examples herein, transgenic animals of the invention that express the human midsized neurofilament gene (NF-M) display pathologies associated with human neurodegenerative disorders, including the formation of neurofibrillary tangles. As is also shown in the working examples, the transgenic animals exhibit a heightened sensitivity to environmental agents, such as aluminum, that are thought to play a role in the progression of some neurodegenerative processes. The transgenic animals of the invention may be used as an economical model system for identifying and/or detecting early manifestations of neurodegenerative disorders and for testing therapeutic treatments and interventions. The transgenic animals may also be used in the study of neuronal degenerations that occur as a normal function of the aging process. Additionally, the transgenic animals may also be utilized in toxicological investigations designed to identify and evaluate environmental factors that contribute to the development of neuropathologies, including, but not limited to, neurofibrillary tangle formation.

2. BACKGROUND OF THE INVENTION

2.1 Neurodegenerative Diseases

Neurodegenerative diseases occur in a large sector of the human population. Alzheimer's disease, alone, affects more than 30% of people over 80 years of age (Evans et al., 1989, JAMA 262:2551–2556; Katsman, R. & Saitoh, T., 1991, FASEB J. 280:278–286). Characteristics of neurodegenerative diseases like Alzheimer's disease, amyotrophic lateral sclerosis, Down's syndrome and Parkinson's disease include the derangement of the cytoskeleton network, aberrant phosphorylation of neurofilaments and of tau proteins, and the accumulation of neurofibrillary material, including tangles, in affected neurons. In addition to the neurodegenerative diseases listed above, neurofilamentous inclusions can also be found in Picks disease, progressive supranuclear palsy, neuronal intranuclear inclusions disease, dementia pugilistica, and other degenerative, metabolic, viral, and toxicologically induced disorders. A small number of tangles are formed in brains of normal elderly people, as well.

Neurofibrillary tangles are composed of an abnormal accumulation of intraneuronal filaments. While abnormal structures, however, the tangle components seem to be derived from normal neuronal elements, including neurofilament subunit proteins and tau proteins, which are microtubule-associated proteins normally present in neurons. Some controversy exists, however, over other possible molecular constituents of the neurofibrillary tangles. For example, some studies suggest that the β/A4 fragment of the amyloid precursor protein (APP) is a component of extraneuronal or "tombstone" neurofibrillary tangles (Hyman, B. T. et al., 1989 Neurosci. Lett. 101:352–355). Generally, neurofibrillary tangles accumulate in the cell bodies of large neurons in the brain, including the pyramidal cells of the hippocampus and neocortex, large neurons of the olfactory cortex, amygdala, basal forebrain nuclei, and several brain stem nuclei.

While a hallmark of many neurodegenerative disorders, such as Alzheimer's disease, most of the diseases in which neurofibrillary tangles occur are peculiar to humans; rodents, for example, do not show these neuropathological changes. Attempts to develop transgenic animal models for Alzheimer's disease have been made (Kawabata et al., 1991, Nature 354:476–478; Kawabata et al., 1991, Nature 356:23; Kawabata et al., 1991, Nature 356:265; Marx, 1991, Science 253:266–267; Quon et al., 1991, Nature 352:239–241; Wirak et al., 1991, Science 253:323–325). The focus of each of these attempts has been to produce mice that exhibit a second, different, hallmark of Alzheimer's disease: extracellular amyloid plaques. These attempts use one or another of several APP constructs as a transgene, but, thus far, the studies have met with limited success, and, in addition, none of the animals have exhibited neurofibrillary pathologies or tangles. To date, in fact, there exist no non-human primate or laboratory rodents that accumulate neurofibrillary tangles in sufficient amounts to be useful as a research tool. This makes the study of early stage disease markers, the search for and evaluation of therapeutic regimens and treatments, as well as the eventual prevention of these disorders extremely difficult.

2.2 Neurofilaments

Neurofilaments (NFs), members of the intermediate filament (IF) class of cytoskeletal element, are the major cytoskeletal components of large diameter axons. The putative roles of axonal NFs include the maintenance of axon caliber and establishment of fast conduction velocity (Hoffman, P. N., et al., 1984, J. Cell Bio. 99:705–714). However, direct evidence for the function of axonal NFs has yet to be obtained. Also, it is not clear if dendritic and perikaryal NFs serve important roles in these neuronal domains.

NFs are composed of three related proteins, the light, midsized, and heavy neurofilament subunits, that are the products of three separate genes. The proteins are designated as NF-L, NF-M, and NF-H, respectively. The three human neurofilament genes have been cloned and encode proteins of molecular masses of 68, 100, and 115 kiloDaltons (kD) (Julien, J. -P., et al., 1987, Genes and Dev. 1:1085–1095; Lees, J. F., et al., 1988, EMBO. J. 7:1947–1955; Myers, M. W., et al., 1987, Embo. J. 6:1617–1626). In addition to the genes encoding human NFs, rodent NF genes have also been isolated and characterized (Julien J. -P. et al., 1988 Gene 68:307–314; Levy et al., 1987, Eur. J. Biochem 166:71–77). Although other neuron-specific IFs such as peripherin (Leonard, D. G. B. et al., 1987, J. Cell Biol. 106:181–193; Portier, M. M. et al., 1984, Dev. Neurosci. 6:335–344), α-internexin (Fliegner, K. H. et al., 1990, Embo. J. 9:749–755), and nestin (Lendahl, U. L. and Zimmerman, L. B., 1990, Cell 60:585:595), have recently been identified in addition to the NF triplet proteins in the mature central nervous system (CNS), NF-L, NF-M, and NF-H appear to be the most abundant and widely expressed neuronal IF proteins.

Each NF subunit contains 4 or 5 easily demarcated, shared protein domains (FIGS. 1A through 1C). A hallmark of intermediate filament proteins, including the neurofilament proteins, is the presence of a highly conserved α-helical, or rod, domain. In the case of the NFs, this region consists of 310–315 amino acid residues. The rod domain is flanked on one side by the amino terminal head domain. This domain is approximately 100 amino acids long and is rich in serine, arginine and the small uncharged amino acids glycine and alanine. The rod domain of each of the NF subunits is flanked on the other side by a glutamate rich region, characterized by an acid:base ratio of >3:1 and a charged:apolar ratio of >1. The function of this domain is unknown at the present time. Carboxyl to the Glu-rich domain, the human NF-M protein contains a multiphosphorylation site with 26 copies of the amino acid triplet lysyl seryl proline (Lys-Ser-Pro, KSP). The KSP repeat has been shown to correspond to the major multiphoshorylation sites of human NF-M (Lee, V. -M. Y. et al., 1988, Proc. Natl. Acad. Sci. USA 85:1998–2002). The NF-H protein also has a multiphosphorylation domain just carboxyl to the Glu-rich domain that contains between 40 and 48 KSP repeats, depending on the animal species. Finally, each of the NF subunits possess carboxy termini that are quite different from each other.

By far the most striking difference between the human and the rodent neurofilament proteins is the presence of a multiphosphorylation site in the human midsize neurofilament NF-M subunit while the cognate rodent proteins have only a single sequence motif resembling the human NF-M KSP sequence. (For reviews, see Shaw, C., 1990, Neurofilament proteins. In R. D. Burgoyne, ed: The Neuronal Cytoskeleton. Wiley-Liss, Inc., N.Y., pp. 183–212; Steinert, P. M. and Roop, D. R., 1988, Ann. Rev. Biochem. 57:593–625).

NF-M is the first neurofilament subunit to appear during embryonic development (Bennett, C. S. and DiLullo, C., 1985, Dev. Biol. 107:107–127; Pachter, J. S. and Leim, R. K. H., 1984, Dev. Biol. 103:200–210; Szaro, B. C., et al., 1989, Dev. Brain Res. 48:87–103; Tohyama, T., et al., 1991, J. Comp. Neurol. 310:285–299) and its sequence is the most highly conserved among the three subunits from diverse animal species. Furthermore, lamprey NFs, which are comprised of a single polypeptide chain, share both immunological and sequence homology with NF-M (Pleasure, S. J., et al., 1989, J. Neurosci. 9:698–709; M. Selzer, personal communication).

NF-L is the most abundant subunit and in vitro experiments have shown that it is capable of assembly in the absence of the other subunits (Geisler, N. and Weber, K., 1981, J. Mol. Biol. 151:565–571; Liem, R. K. H. and Hutchinson, S. B., 1982, Biochemistry 21:3221–3226). The NF-L subunit differs most significantly from the other two NF subunits in that it lacks the extended carboxy terminal tails found in both NF-M and NF-H (Sharp, G. A. et al., 1982, Exp. Cell Res. 137:403–413; Hirokawa, N. M. et al., 1984, J. Cell Biol. 98:1523–1536; Hisanaga, S. -I. and Hirokawa, N., 1988, J. Mol. Biol. 202:297–305). It has been suggested that NF-L is an integral component of the neurofilament backbone (Hirokawa, N. M. et al., 1984, J. Cell Biol. 98:1523–1536), while NF-H, and possibly NF-M are involved in the formation of neurofilament cross-bridges (Hirokawa, N. M. et al., 1984, J. Cell Biol. 98:1523–1536; Hisanaga, S. -I. and Hirokawa, N., 1988, J. Mol. Biol. 202:297–305). Sequence determination for NF-M (Myers, M. W. et al., 1987, EMBO J. 6:1617–1626) and NF-H (Julien, J. -P., et al., 1987, Gene 68:307–314; Lees, J. F., et al., 1988, EMBO J. 7:1947–1958), however, strongly suggest that NF-M and NF-H are integral components of the NF backbone as well.

Although each of the human NF genes has been expressed in tissue culture systems, attempts at using transgenic animals to assess the functions of the NF subunits have met with limited results. For example, transgenic animals containing human NF-L have been made, but no overt phenotypes relative to nontransgenic littermates have been observed (Julien, J. -P. et al., 1987, Genes and Dev. 1:1085–1095). A recent account by Cote et al. describes transgenic animals containing human NF-H, but again, no overt phenotype is reported (Cote, F. et al., 1991, (abs.) J. Cell Biol. 115:163a). Some transgenic mouse lines have been produced that accumulate abnormally high levels of the murine NF-L in several tissues, neural as well as nonneural (Montiero, M. J., 1990, J. Cell Biol. 111:1543–1557). Although the neurons of some of these animals have been shown to contain a greater number of neurofilaments than the wild type, they do not exhibit an increase in axon diameter. Thus, even overexpression of the protein fails to elicit any severe effect. A recent abstract describes transgenic mice that produce high levels of the murine NF-L, again in an abnormal pattern of tissue expression (i.e., in both neural and nonneural tissues). These mice show some morphologic and biochemical effects of this expression: the displacement of the nucleus and the accumulation of phosphorylated forms of NF-H (Xu, Z. -S. et al., 1991, (abs.) J. Cell Biol. 115:163a). Attempts to study NF-M function by engineering transgenic mice that express NF-M have met with as little success as the NF-L and NF-H studies. Mice carrying truncated versions of the murine NF-M protein have reportedly been engineered but no overt phenotype is observed in these animals (Wong, P. C. et al., 1991, (abs.) J. Cell Biol. 115:122a).

3. SUMMARY OF THE INVENTION

Transgenic animals which may be suitable animal model systems for neurodegenerative disorders are described. The transgenic animals of the invention are engineered using regulatory nucleotide sequences that drive neuron-enriched expression of the human neurofilament subunit protein, NF-L, NF-M, or NF-H. The examples described herein demonstrate that the presence of even low levels of the human NF-M protein, for example, with its unique multiphosphorylation repeats, produces dramatic neuropathological results in the transgenic animals. In an embodiment of the invention described in the working examples herein, a human NF-M transgene regulated by human NF-M promoter sequences is expressed in neural tissue. This neuronal expression of the human NF-M protein is sufficient to produce intracellular neurofibrillary pathology similar to that found with several neurodegenerative disorders, such as Alzheimer's disease, Parkinson's disease, and amyotrophic lateral sclerosis, to name but a few. In addition, it is demonstrated that transgenic expression of NF-M produces an increased sensitivity to environmental factors, such as aluminum, that are thought to be important in the progression of some neurodegenerative processes.

The transgenic animals of this invention are the first to be designed and produced that accumulate neurofibrillary materials, including tangles, characteristic of many neurodegenerative disorders, in sufficient quantity to be useful as a research tool. Thus, the transgenic animals of this invention represent a significant advance toward the design and construction of a suitable model for these disorders. The transgenic animals of the invention may be used as economical animal model systems for the study of early manifestations of neurodegeneration; both abnormally induced degenerations as well as those that occur as a normal function of the aging process. Further, the transgenic animals can provide a test system for the evaluation of strategies for diagnosis, prevention or therapeutic intervention. In addition, the animals may also be utilized in toxicological investigations designed to identify and evaluate environmental factors that contribute to the development of neuropathologies such as neurofibrillary tangle formation.

4. BRIEF DESCRIPTION OF THE FIGURES

FIGS. 1A–1C: Organization of NF subunits. (FIG. 1A) NF-L; (FIG. 1B) NF-M; (FIG. 1C) NF-H. (Adapted from Lees J. F. et al., 1988, EMBO J. 7:1947–1955).

Figure 2B:
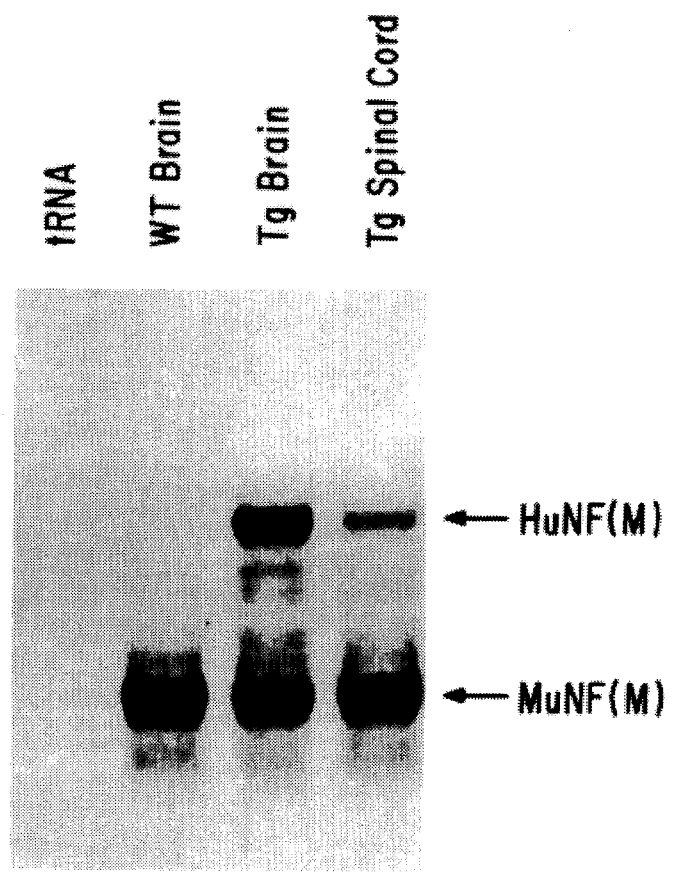

FIGS. 2A–2B: Expression of Human NF-M mRNA in transgenic tissues. RNAase protection assays were performed as described in Section 6.1.2, RNA Analysis. In (FIG. 2A) 250,000 CPM of a human NF-M specific probe and 50,000 CPM of a murine β-actin probe were hybridized with 10 μg of total cellular RNA from the indicated tissues of a 10 month old transgenic (Tg) mouse, 10 μg of RNA from the brain of a wild-type (WT) non-transgenic littermate or 10 μg of yeast tRNA. Protected fragments were analyzed on a 6% polyacrylamide/7M urea sequencing gel. Positions of the human NF-M and murine β-actin protected fragments are indicated. In (FIG. 2B), the levels of expression of the endogenous murine NF-M gene and the human NF-M transgene were compared in a 4 month old transgenic animal. 50,000 CPM each of human NF-M and murine NF-M specific probes were hybridized with 10 μg of yeast tRNA, 10 μg of wild type or transgenic brain RNA or 2.5 μg of transgenic spinal cord RNA. Protected fragments were separated as double-stranded RNA on a 6% native polyacrylamide gel. Exposures were done with an intensifying screen for 72 hrs in (FIG. 2A) or 12 hrs in (FIG. 2B).

Figure 3A:
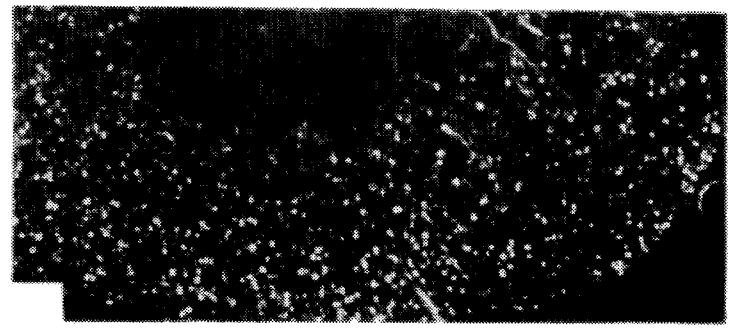
Figure 3B:
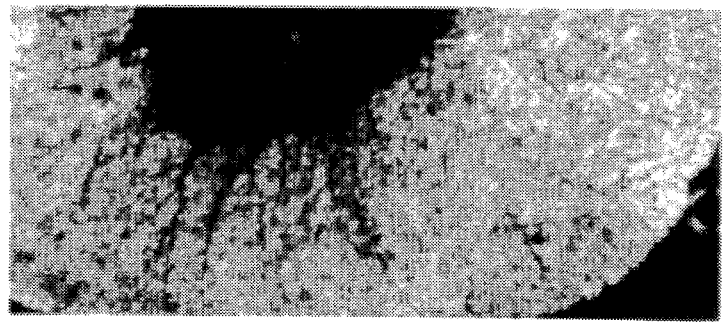
Figure 3C:
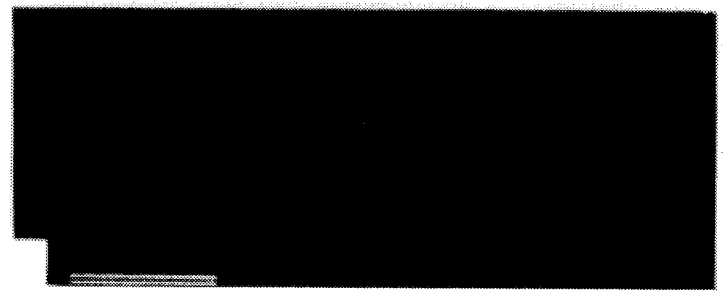
Figure 3D:

FIGS. 3A–3D: (FIG. 3A) Spinal cord sections of a transgenic mouse stained by indirect immunofluorescence with H014, a MAb specific for human NF-M. (FIG. 3B). Same section as (FIG. 3A) viewed with polarized light to show location of white matter. (FIG. 3C). Wild type mouse spinal cord section stained with H014. Note that this MAb specifically recognizes human but not mouse NF-M. (FIG. 3D) Same section as in (FIG. 3C), viewed with polarized light. Scalebar, 200 μm.

Figure 4A:
Figure 4B:
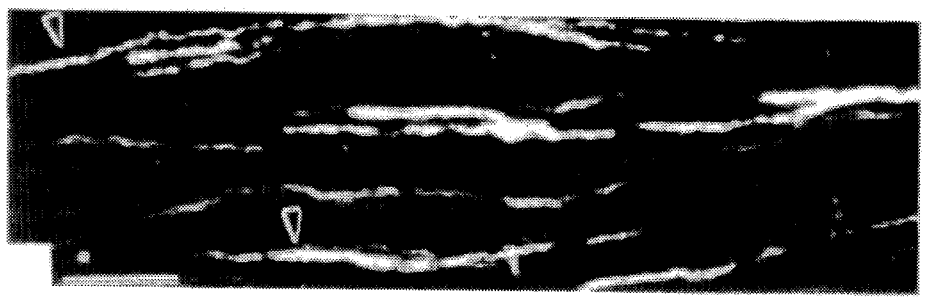

FIGS. 4A–4B: Spinal cord sections of transgenic mouse stained by two color immunofluorescence with MAb specific for human NF-M (H014) (FIG. 4A) or MAb specific for mouse NF-M (RM0108) (FIG. 4B). Note that the same axons are stained by both MAbs. Scalebar, 50 μm.

Figure 5:
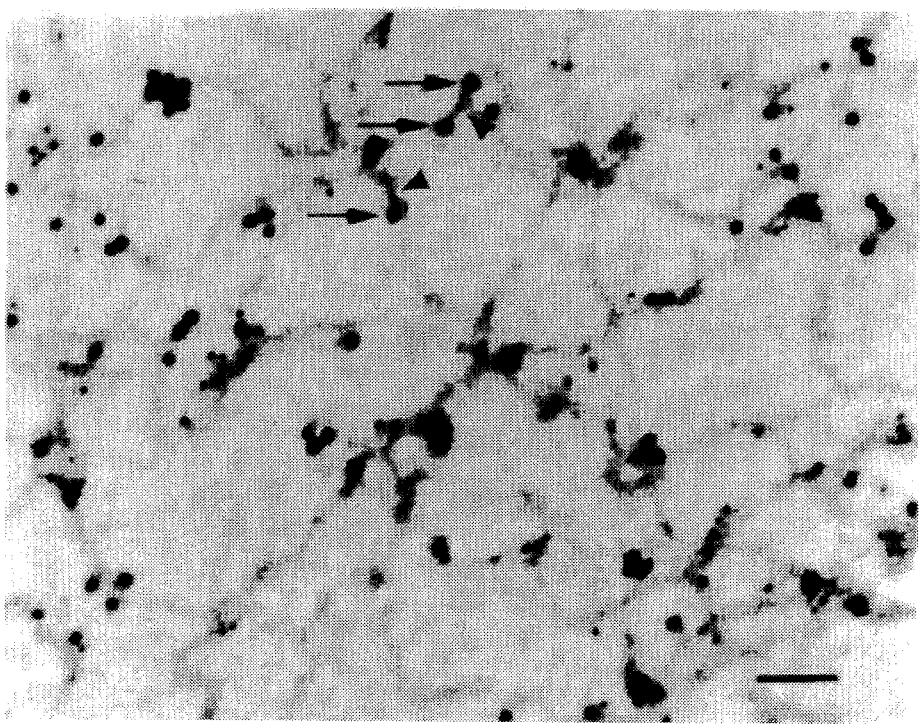

FIG. 5: Double immunolabeling of enriched isolated NFs from transgenic mice. Human NF-M is revealed with an anti-human specific MAb, H014 (10 nm gold particles) and mouse NF-M is revealed with an anti-mouse specific MAb, RM0108 (5 nm gold particles). Note that both size particles can be detected on the same filament. Scalebar, 250 μm.

Figure 6A:
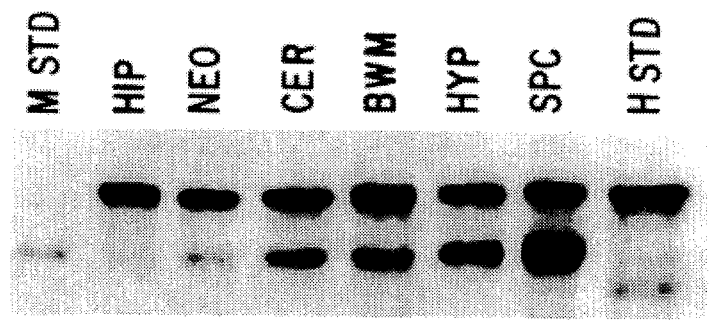
Figure 6B:
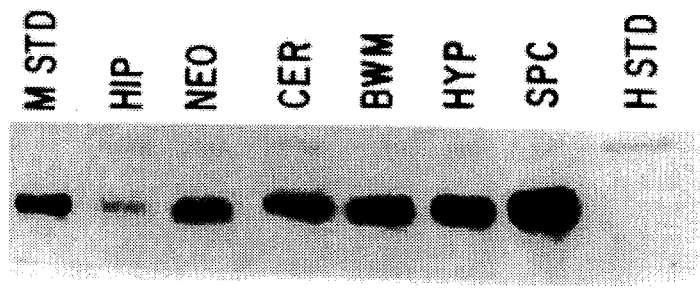

FIGS. 6A–6B: Quantitative Western blotting of 6 different regions of nervous system tissue. The regions analyzed were: HIP=hippocampus, NEO=neocortex, CER=cerebellum, BWM=brain white matter, HYP=hypothalamus, SPC=spinal cord. In FIG. 6A, lane labeled M contains 45 ng of the 145 kD mouse NF-M standard and lanes labeled H contains 250 ng of the 170 kD corrected human NF-M standard. 45 μg of total protein was loaded in each lane of a 6% gradient SDSPAGE gel. In FIG. 6A, the nitrocellulose replica was probed with RM0254 which has a higher affinity for human NF-M than mouse. In FIG. 6B, an identical nitrocellulose replica was probed with RM0292. The amount of mouse NF-M standard loaded was 250 ng and the amount of human NF-M loaded was 90 ng. The latter MAb shows remarkably less immunoreactivity for human NF-M which, when calculated using human and mouse NF-M standards, represents a closer approximation of the actual levels of human and mouse NF-M in the tissue.

Figure 7:
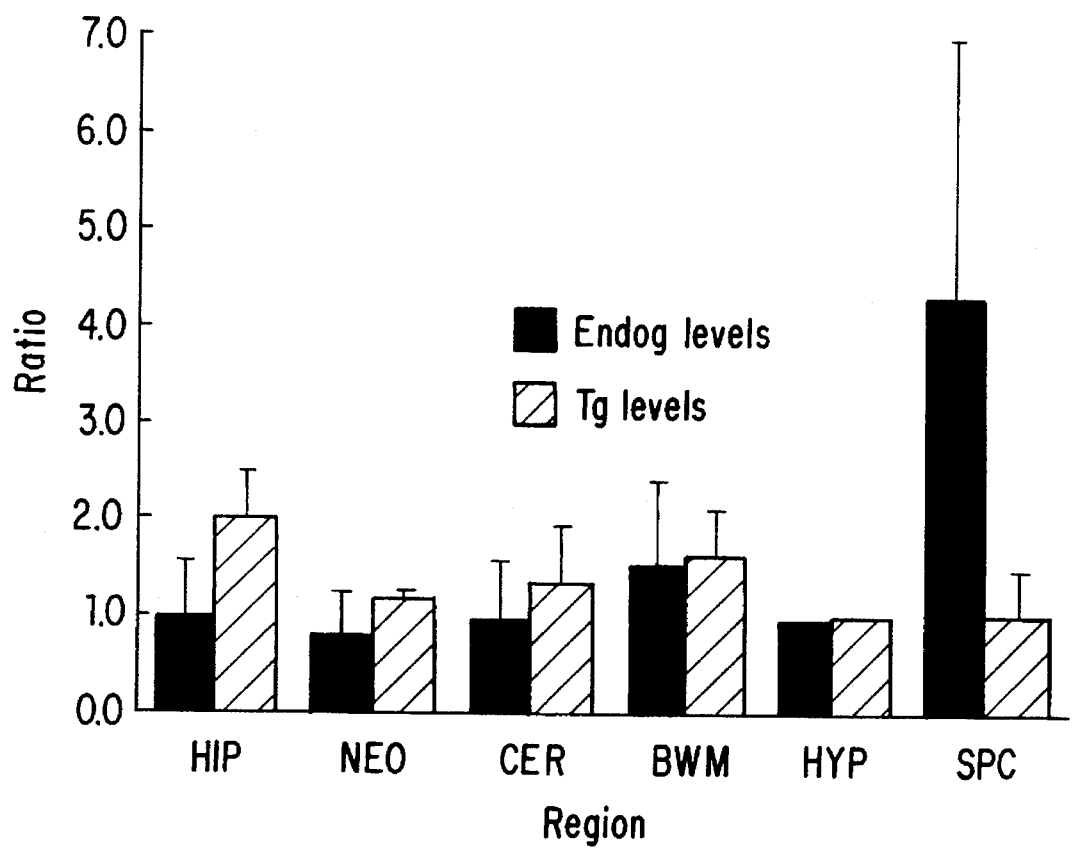

FIG. 7: Distribution of transgenic human and endogenous mouse NF-M proteins in transgenic mice. 45 μg of total tissue homogenates of the 6 different regions was loaded per lane and probed with RM0254. CPMs, corrected for background of transgenic and endogenous NF-M proteins in the six regions were compared to the CPM obtained for the hypothalamus. The bars represent the ratio of each region versus hypothalamus. The lines above each bar show the standard deviation of the samples. Abbreviation for each CNS region is the same as FIGS. 6A–6B.

Figure 8:
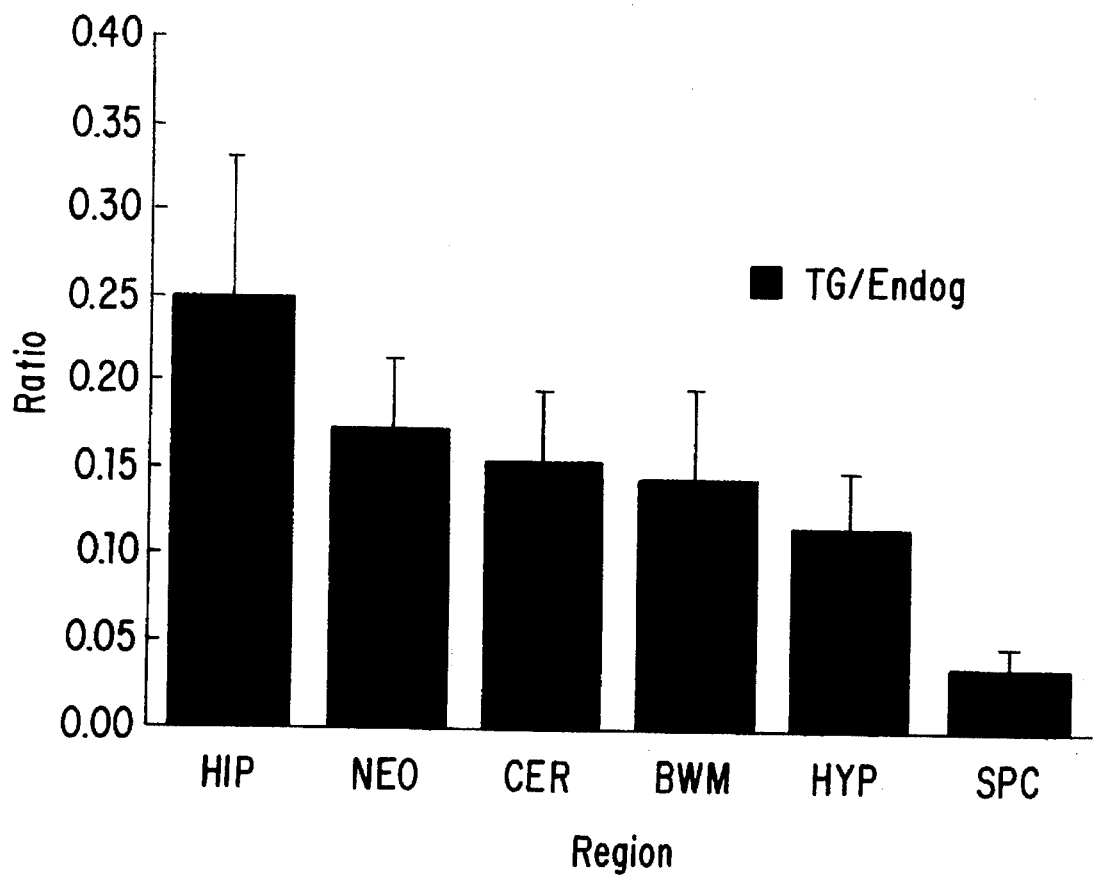

FIG. 8: Ratio of transgenic human to endogenous mouse NF-M proteins in transgenic mice. Abbreviation for each CNS region is the same as for FIGS. 6A–6B. Conditions for loading and Western blotting with RM0254 are described as for FIG. 7. To calculate the ratio of human and mouse NF-M expressed, a conversion factor based on the affinity of the MAb for human and mouse NF-M was generated using the CPM bound to known amounts of mouse and human NF-M standards. Ratios were generated for HIP based on 44 observations in 9 animals; NEO: 44 observations in 9 animals; CER: 31 observations in 8 animals; BWM: 23 observations in 4 animals; HYP: 27 observations in 4 animals; SPC: 41 observations in 9 animals. The line above each bar represent the standard deviation of the samples.

Figure 9:
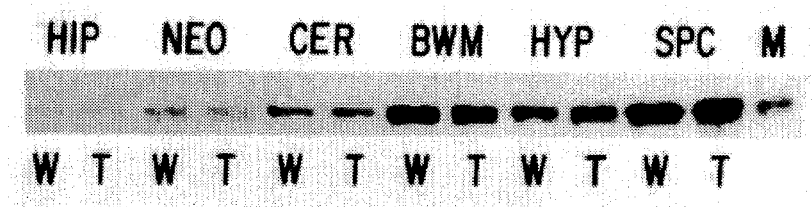

FIG. 9: Comparison of mouse NF-M in transgenic and wild type mice. 45 μg of total proteins from the same regions as described in FIGS. 6A–6B were loaded on 7.5% acrylamide gels and probed with RM0255. Comparison of CPM between wild type and transgenic mice shows maintenance of levels of endogenous NF-M.

Figure 10A:
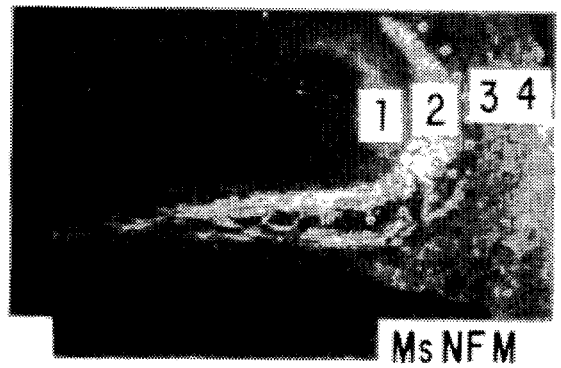
Figure 10B:
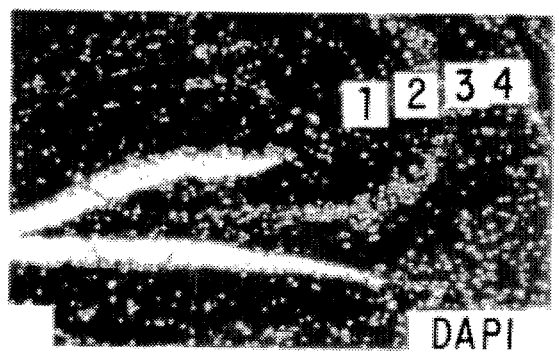
Figure 10C:
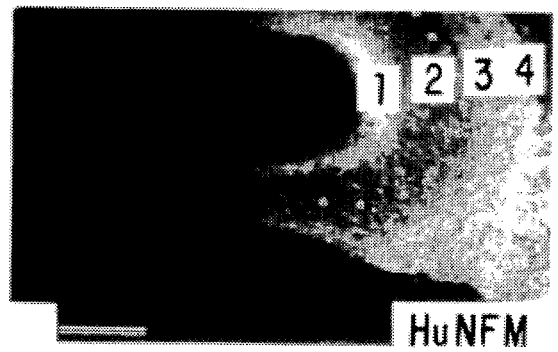

FIGS. 10A–10C: Distribution of murine (FIG. 10A) and human (FIG. 10C) NF-Ms in hippocampus of transgenic mouse. A cryostat section was stained by simultaneous two-color immunofluorescence for murine (mouse MAb RM0108) and transgenic human (rat MAb H014) NF-Ms and counterstained with the nuclear dye DAPI. The identical field is illustrated in the three panels, showing (FIG. 10A) fluorescein, (FIG. 10B) DAPI, or (FIG. 10C) rhodamine fluorescence. Dots, pyramidal cell layer. Markers 1–4 are placed identically in the three panels to aid comparison. Scale Bar 200 μm.

Figure 11A:
Figure 11B:
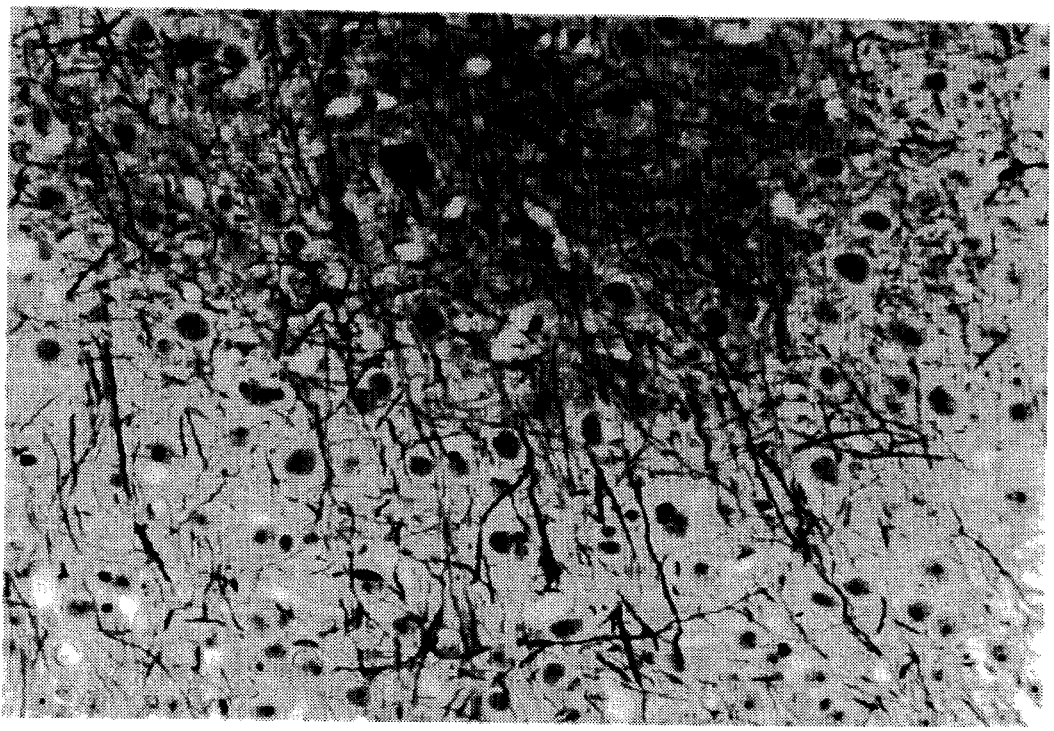
Figure 11C:
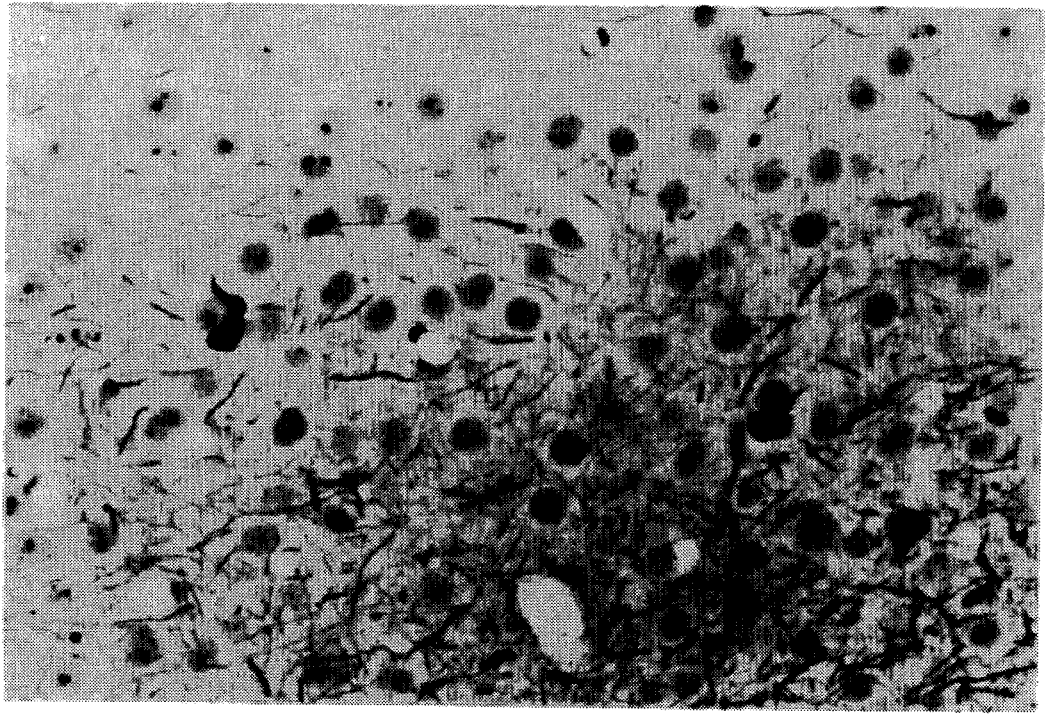

FIGS. 11A–11C: Neurofibrillary pathology in the central nervous system of transgenic mice. Tissue sections from brains of a 4.6 month old and a 27 month old human NF-M transgenic mice (NF-M 27). FIG. 11A shows a section of the anterior cerebral cortex (olfactory bulb above) that is visualized by indirect immunofluorescence using monoclonal antibody H014. The neurofibrillary accumulations appear as bright dots of differing size. FIGS. 11B–11C shows a section of brain stained by silver the impregnation method of Bielschowsky. Several neuropathologies, including neurofibrillary tangles and pick-like bodies are present in a single high magnification microscope field.

Figure 12A:
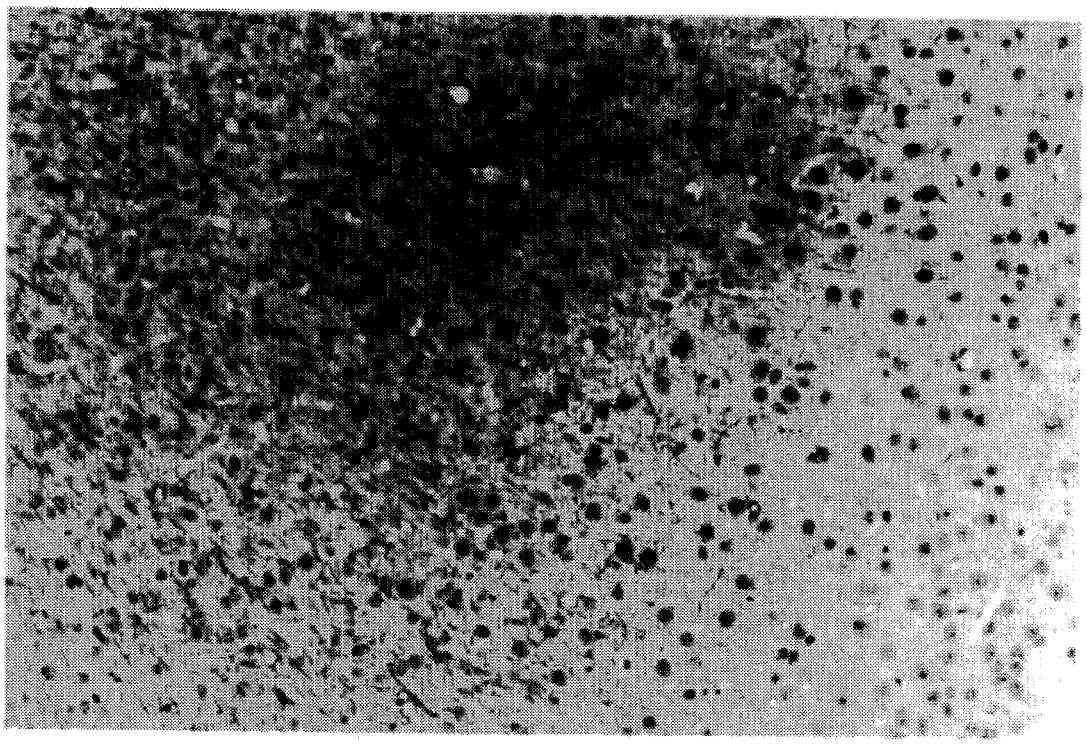
Figure 12B:
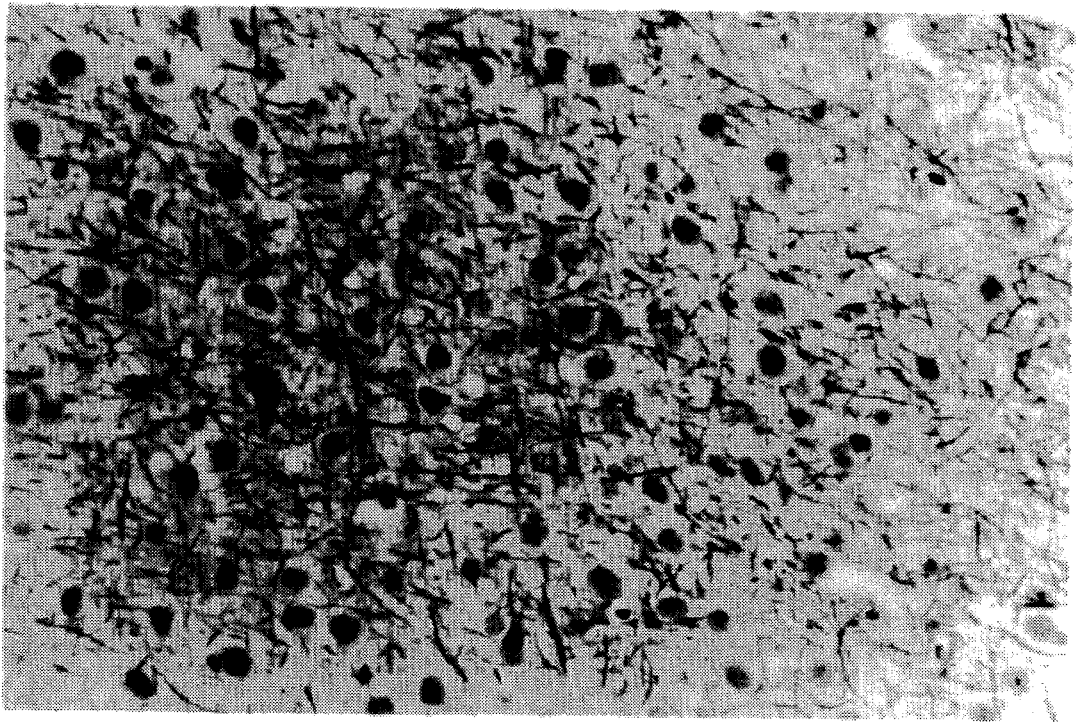
Figure 12C:
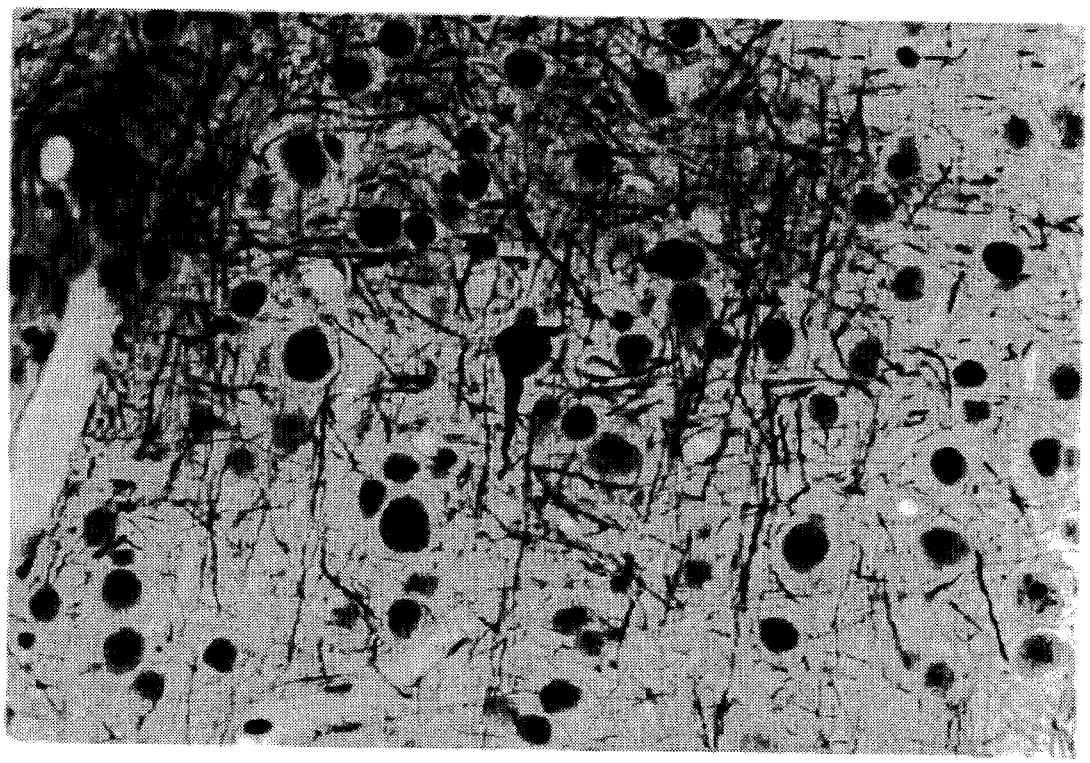
Figure 12D:
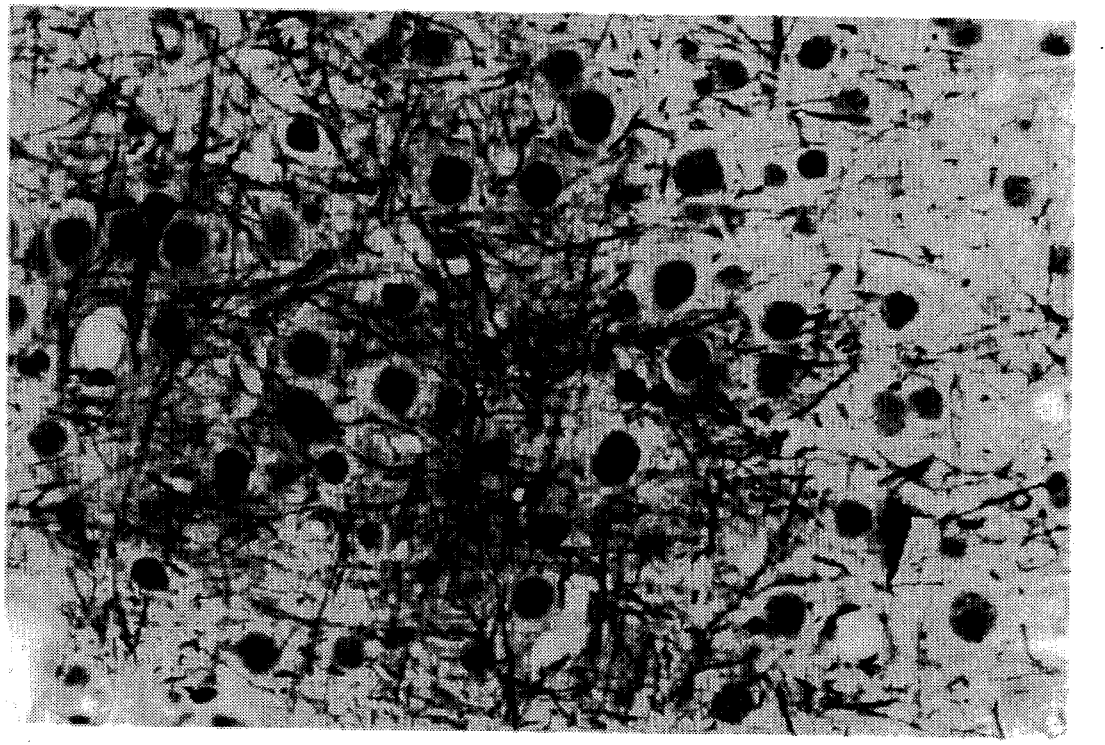

FIGS. 12A–12D: Effects of aluminum treatment on tangle formation in transgenic and wild type mice. Tissue sections from brains of 3 month old aluminum-treated mice. FIGS. 12A–12B. Wild type FIGS. 12C–12D. Human NF-M transgenic (NF-M 27). Note presence of neuropathologies.

FIG. 13: Table summarizing effects of aluminum treatment on 3 month old wild type and NF-M mice.

Figure 14A:
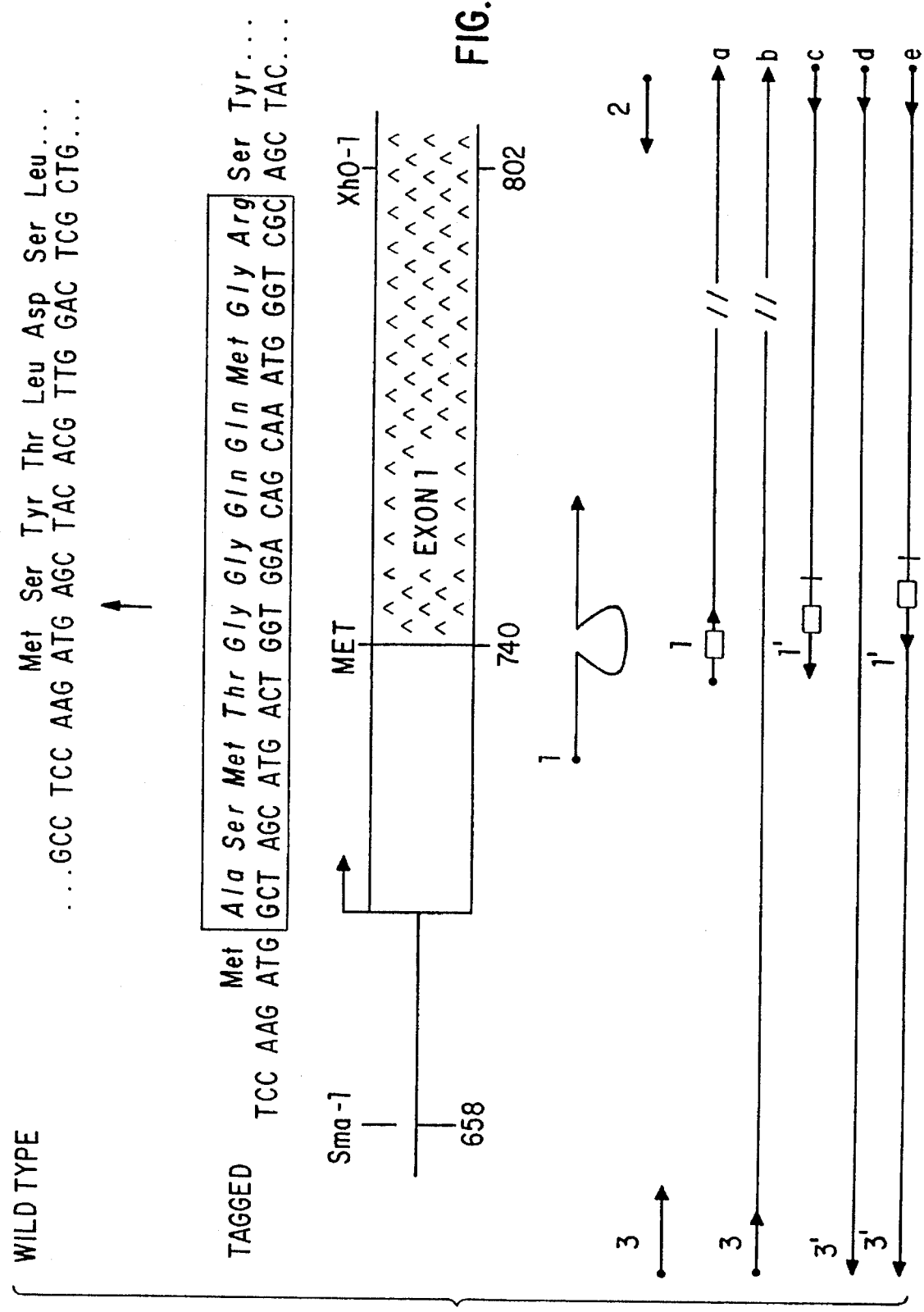
Figure 14B:
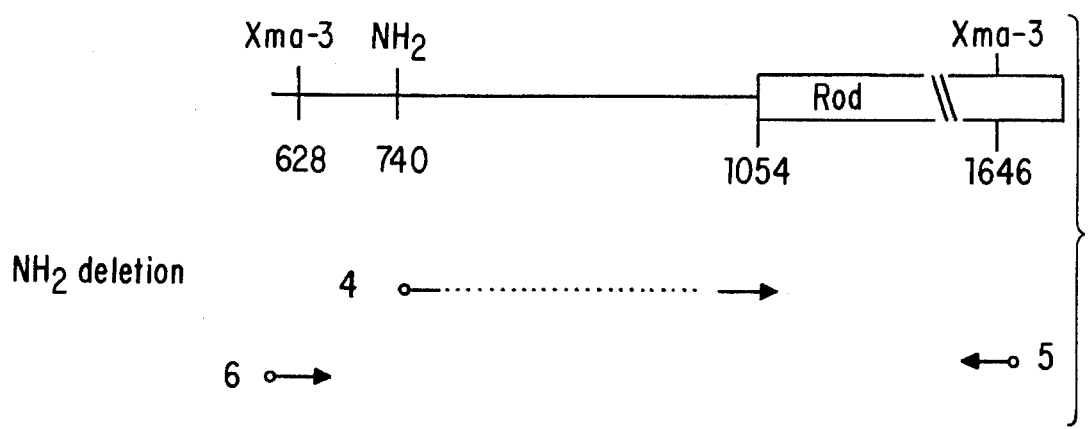
Figure 14C:
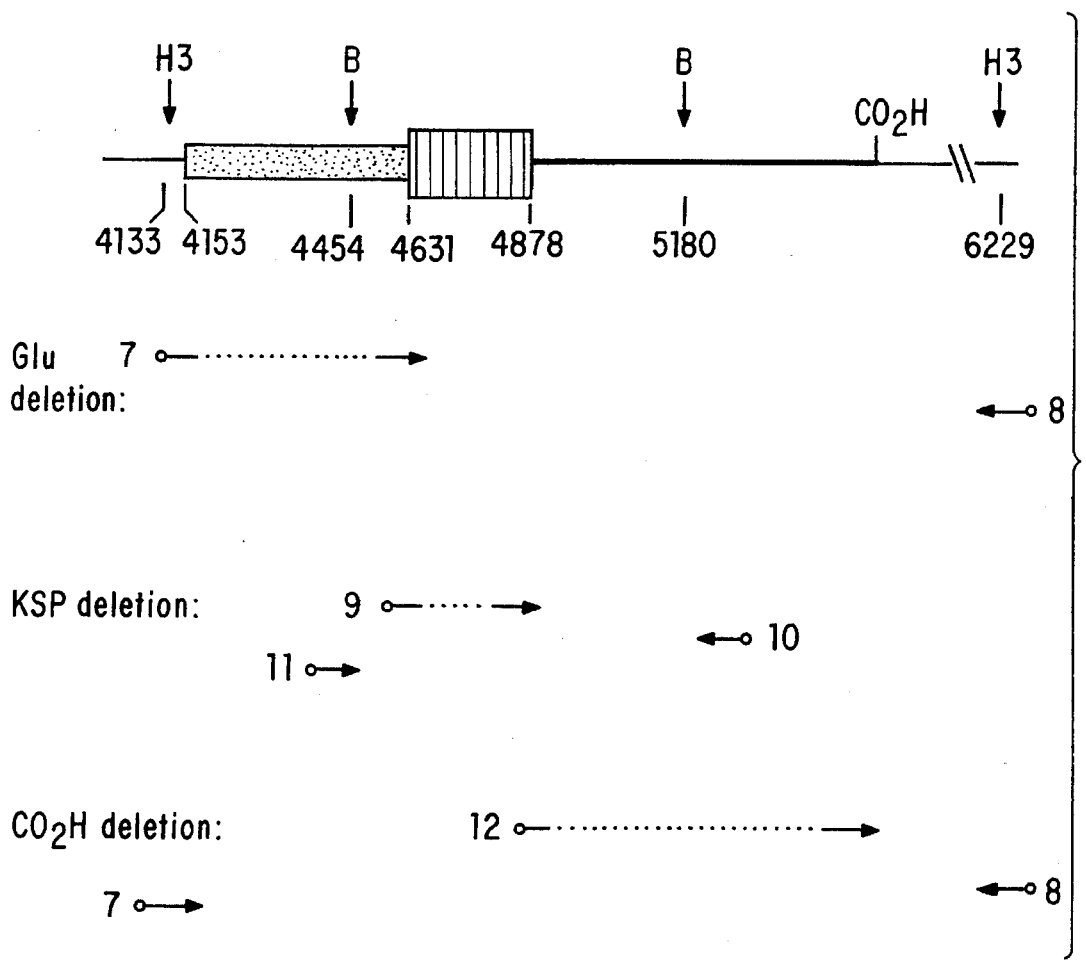

FIGS. 14A–14C: Schematic diagram of portions of the NF-M gene and the method for altering these portions by PCR. The nucleotide sequences of the primers correspond to those of the indicated region of the gene. Arrow heads represent 3' termini and filled circles represent 5' termini of the primers. Dotted lines represent sequences not included in the primers. The heavy loop in primer 1 corresponds to the 33 nucleotides encoding the "tag" (stippled amino acid sequence). FIG. 14A. Preparation of the tagged NF-M; FIG. 14B. Amino terminal domain deletion; FIG 14C. Glu-rich, KSP and carboxy terminal domain deletions.

5. DETAILED DESCRIPTION OF THE INVENTION

The present invention involves the design, construction and use of transgenic animals which exhibit pathological features of human neurodegenerative disorders. These features include, but are not limited to, the accumulation of neurofibrillary material, including tangles, as the animals age. In addition, the animals exhibit a marked sensitivity to certain environmental agents, such as aluminum, that are thought to be important in the progression of some neurodegenerative processes. The founder transgenic animals of the invention are produced by methods well known in the art for the introduction of heterologous genes into animal systems, and consist of animals in which said heterologous gene expresses all or any part of one or more of the human neurofilament subunit (NF-L, NF-M, NF-H) peptides in a neuron-enriched manner (referred to herein as "NF transgenic animals")

In accordance with the invention, transgenic animals which exhibit such pathologies may be used to study many neurodegenerative processes. They may be used to identify markers (e.g., genetic, enzymatic, or biochemical markers) of early degenerative stages that could then be useful in human diagnostics; to evaluate drugs, pharmaceuticals, treatments and intervention regimens for the prevention or treatment of neurodegenerative diseases and disorders in which these neuropathological symptoms occur; and to screen agents that may exacerbate the progression of such disorders.

The invention also involves the design and production of transgenic animals that may be crossbred with the NF transgenic animals in order to assess the effect of other gene products, e.g., other neurospecific IFs, and other possible neurofibrillary tangle components such as tau proteins or the β/A4 fragment of the amyloid precursor protein (APP) (Kang et al., 1987, Nature 325:733–736) on the course of neuropathologic progression.

The following aspects of the invention are explained in the subsections below, solely for purposes of description and not by way of limitation: the human NF sequences, and vectors and promoters that can be used in conjunction with human NF sequences in the construction of chimeric transgenes for engineering the transgenic animals of the invention; methods for producing animals and establishing colonies by inbreeding or crossbreeding; and uses of the transgenic animals as model systems for neurodegenerative diseases, including but not limited to Alzheimer's disease.

5.1 Human NF-M Transgene

DNA containing the nucleotide coding sequence for the entire human NF-M protein, or any portion thereof may be used to produce the transgenic animals of the invention. Due to the degeneracy of the genetic code, other DNA sequences which encode substantially the same NF-M protein or a functional equivalent can also be used. The nucleotide coding sequence used to produce the transgenic animals of the invention is regulated by human NF-M promoter regulatory nucleotide sequences. These regulatory sequences may include the entire, or any portion of, the NF-M promoter. Alternatively, chimeric gene constructs containing the nucleotide coding sequence for the entire human NF-M, or any portion thereof, regulated by another neuron-specific or neuron-enriched promoter or promoter/enhancer complex may be engineered as the transgene to be used in the production of the transgenic animals of the invention. Multiple copies of the chimeric gene construct may be arranged in the vector, and multiple copies of the human NF-M gene or chimeric gene construct may be stably introduced into the transgenic founder animals.

Human NF-M nucleotide coding sequences (Myers et al., 1987, EMBO J. 6:1617–1626, which is incorporated by reference herein in its entirety) may be used that yield protein variants including, but not limited to NF-M proteins containing: a portion of, a deletion of, or multiple copies (i.e., greater than one) of, the head domain, consisting of amino acid residues 1 to about 100, the rod domain, ranging from about amino acid residue 100 to about amino acid residue 419, the glutamic acid-rich domain, ranging from about amino acid residue 455 to about amino acid residue 611, the multiphosphorylation site domain, ranging from about amino acid residue 614 to about amino acid residue 691, and/or the tail domain, ranging from about amino acid residue 692 to about amino acid residue 916. In addition, mutations can be introduced into the human NF-M nucleotide coding sequence which yield one or more amino acid substitutions and/or insertions into the resulting human NF-M protein. These substitutions and/or insertions can exist simultaneously in one or more of the head, rod, glutamic acid-rich, multiphosphorylation, and/or tail domains. Further, the substitutions and/or insertions can be engineered into any of the protein variants described supra that have portions of, deletions of, and/or multiples copies of one or more of the domains listed. Optionally, a short heterologous amino acid "tag" may be attached to any of the resulting protein variants such that said variants may be identified immunocytochemically, irrespective of the NF-M regions modified or deleted. Any of the human NF-M nucleotide coding sequences that will yield any of the protein variants described can be produced using recombinant DNA and cloning methods which are well known to those skilled in the art and are described infra.

Regulatory nucleotide sequences that comprise the entire, or any portion of, the human NF-M promoter (Myers, M. W. et al., 1987, EMBO. J. 6:1917–1926) may be used to drive the expression of any of the nucleotide coding sequences that will yield any of the protein variants described supra. Alternatively, chimeric gene constructs may be produced in which the nucleotide regulatory sequences used to drive the expression of any of the nucleotide coding sequences that will yield any of the protein variants described supra may include but are not limited to: the entire, or any portion of the endogenous NF-M promoter of the founder animal into which the human NF-M gene is being introduced, or any other promoter sequences that drive neuron-enriched expression including, but not limited to such promoters as the NF-L (Julien, J. -P. et al., 1987 Genes and Dev. 1:1085–1095, NF-H (Lees, J. F. et al., 1988, EMBO. J. 7:1947–1955), NSE (neural specific enolase) (Forss-Petter, S. et al., 1990, Neuron 5:187–197), APP (Wirak et al., 1991, Science 253:323–325), or Thy-1 (Gordon, J. et al., 1987, Cell 50:445–452; Kollias et al., 1987, Proc. Natl. Acad. Sci. USA 84:1492–1496; Vidal et al., 1990, EMBO J. 9:833–840) promoters. Any functionally equivalent promoters or promoter/enhancer complexes may be used.

In order to produce the gene constructs used in the invention, recombinant DNA and cloning methods which are well known to those skilled in the art may be utilized (see Sambrook et al., 1989, Molecular Cloning, A Laboratory Manual, 2nd Ed., Cold Spring Harbor Laboratory Press, NY). In this regard, appropriate NF-M coding sequences may be generated from human NF-M cDNA or genomic clones using restriction enzyme sites that are conveniently located at the relevant positions within the NF-M sequence. Alternatively, or in conjunction with the method above, site directed mutagenesis techniques involving, for example, either the use of vectors such as M13 or phagemids, which are capable of producing single stranded circular DNA molecules, in conjunction with synthetic oligonucleotides and specific strains of *Escherichia coli* (*E. coli*) (Kunkel, T. A. et al., 1987, Meth. Enzymol. 154:367–382) or the use of synthetic oligonucleotides and PCR (polymerase chain reaction) (Ho et al., 1989, Gene 77:51–59; Kamman, M. et al., 1989, Nucl. Acids Res. 17:5404) may be utilized to generate the necessary NF-M nucleotide coding sequences. Human NF-M nucleotide regulatory sequences may be obtained from human NF-M genomic clones utilizing the same techniques. Appropriate NF-M sequences may then be isolated, cloned, and used directly to produce transgenic animals. The sequences may also be used to engineer the chimeric gene constructs that utilize regulatory sequences other than the human NF-M promoter, again using the techniques described here. These chimeric gene constructs would then also be used in the production of transgenic animals.

In an alternative embodiment of the invention, chimeric gene constructs which include entirely different genes may be utilized to create transgenic animals that can be crossbred with the human NF-M transgenic animals of the invention in order to determine the effects of the expression of such genes on the progression of the neuropathologies that are a feature of the invention. For example, the effects of interactions between other neuro-specific IFs with any of the human NF-M proteins described supra may be assessed in the transgenic animal model systems. To this end, for example, a chimeric gene composed of all or part of the coding sequence for peripherin, α-internexin, or nestin, controlled by a neuron-enriched promoter such as the NF-L, NF-M, or NF-H promoters, described supra, can be produced. Any of the NF-L or NF-H gene constructs described in Section 5.2 may be used as well. In addition, the effects of interactions between other known or potential neurofibrillary tangle components with any of the human NF-M proteins described supra may also be assessed in the transgenic animal model systems. To this end, for example, a chimeric gene composed of all or part of the coding sequence for APP or the APP β/A4 fragment, or tau protein (Frubin, D. G. et al., 1984, J. Cell. Biol. 98:1090–1097; Himmler, A. et al., 1989, Mol. Cell. Biol. 9:1381–1388), controlled by a neuron-enriched promoters such as the NF-L, NF-M or NF-H promoters, described supra, may be produced. The use of such transgenes to produce transgenic animals will result in animals that overexpress, in a neural-specific manner, whichever of these coding sequences is present on the transgenic construct. The effects of such transgenic IF, β/A4, or tau protein expression on the progression of neurodegenerative pathologies can be assessed by crossbreeding such transgenic animals with any of the NF-M transgenic animals.

In yet another embodiment of the invention, transgenic animals may be produced in which the function of one or more endogenous genes have been disrupted. These transgenic animals can then be crossbred with the human NF-M transgenic animals of the invention in order to determine the effects that the lack of expression of such endogenous genes has on the progression of the neuropathologies that are a feature of the invention. For example, the disruption of one or more of the endogenous neural-specific IFs such as NF-L, NF-M, NF-H, peripherin, α-internexin and nestin can be assessed. Alternatively, the disruption of proteins that may modify human NF-M, such as a neurofilament-specific protein kinase (Julien, J. -P. and Mushynski, W. E., 1983, J. Biol. Chem. 258:4019–4025; Pierre, M. et al., 1985, Ann. NY Acad. Sci. 455:808–811; Wible, B. A. et al., 1989, Proc. Natl. Acad. Sci. USA 86:720–724), can be studied. In addition, the disruption of endogenous genes encoding components of neurofibrillary tangles, such as tau proteins, may be assessed. To accomplish these endogenous gene disruptions, the technique of site-directed inactivation via gene targeting (Thomas, K. R. and Capecchi, M. R., 1987, Cell 51:503–512) may be used. Briefly, vectors containing some nucleotide sequences homologous to the endogenous gene of interest are designed for the purpose of integrating, via homologous recombination with chromosomal sequences, into and disrupting the function of, the nucleotide sequence of said endogenous gene. The effects of such disruptions of endogenous gene function on the progression of neurodegenerative pathologies can be assessed by crossbreeding such transgenic animals with any of the NF-M transgenic animals.

5.2 Other Human NF Transgenes

DNA containing the nucleotide coding sequences for the entire human NF-L or NF-H proteins, any portions thereof, or, due to the degeneracy of the genetic code, other DNA sequences which encode substantially the same NF-L or NF-H proteins, functional equivalents thereof, regulated by human NF-L or NF-H promoter regulatory nucleotide sequences, respectively, may be used to produce the transgenic animals of the invention. These regulatory sequences may include the entire, or any portion of, the NF-L or NF-H promoters. Alternatively, chimeric gene constructs containing the nucleotide coding sequences for the entire human NF-L or NF-H or any portions thereof, regulated by another neuron-specific or neuron-enriched promoter or promoter/enhancer complex may be engineered as the transgene to be used in the production of the transgenic animals of the invention. Multiple copies of the chimeric gene construct may be arranged in the vector, and multiple copies of the human NF-L or NF-H genes or chimeric gene constructs may be stably introduced into the transgenic founder animals.

Human NF-L nucleotide coding sequences (Julien, J. -P. et al., 1987, Biochim. Biophys. Acta 909:10–20. which is incorporated by reference herein in its entirety) may be used that yield protein variants including, but not limited to NF-L proteins containing: a portion of, a deletion of, or multiple copies (i.e., greater than one) of, the head domain, consisting of amino acid residues 1 to about 100, the rod domain, ranging from about amino acid residue 100 to about amino acid residue 410, and/or the glutamic acid-rich domain, ranging from about amino acid residue 460 to about amino acid residue 555. In addition, mutations can be introduced into the human NF-L nucleotide coding sequence which yield one or more amino acid substitutions and/or insertions into the resulting human NF-L protein. These substitutions and/or insertions can exist simultaneously in one or more of the head, rod, tail, or glutamic acid-rich domains. Further, the substitutions and/or insertions can be engineered into any of the protein variants described supra that have portions of, deletions of, and/or multiples copies of one or more of the domains listed. Optionally, a short heterologous amino acid "tag" may be attached to any of the resulting protein variants such that said variants may be identified immunocyto-chemically, irrespective of the NF-L regions modified or deleted.

Human NF-H nucleotide coding sequences (Lees, J. F. et al., 1988, EMBO J. 7:1947–1955, which is incorporated by reference herein in its entirety) may be used that yield protein variants including, but not limited to NF-H proteins containing: a portion of, a deletion of, or multiple copies (i.e., greater than one) of, the head domain, consisting of amino acid residues 1 to about 100, the rod domain, ranging from about amino acid residue 100 to about amino acid residue 410, glutamic acid-rich domain, ranging from about amino acid residue 439 to about amino acid residue 500, the multiphosphorylation site domain, ranging from about amino acid residue 502 to about amino acid residue 823, and/or the tail domain, ranging from about amino acid residue 825 to about amino acid residue 1020. In addition, mutations can be introduced into the human NF-H nucleotide coding sequence which yield one or more amino acid substitutions and/or insertions into the resulting human NF-H protein. These substitutions and/or insertions can exist simultaneously in one or more of the head, rod, glutamic acid-rich, multiphosphorylation or tail domains. Further, the substitutions and/or insertions can be engineered into any of the protein variants described supra that have portions of, deletions of, and/or multiples copies of one or more of the domains listed. Optionally, a short heterologous amino acid "tag" may be attached to any of the resulting protein variants such that said variants may be identified immunocyto-chemically, irrespective of the NF-H regions modified or deleted.

Regulatory nucleotide sequences that comprise the entire, or any portion of, the human NF-L or NF-H promoters may be used to drive the expression of any of the nucleotide coding sequences that will yield any of the NF-L or NF-H protein variants, respectively, described supra. Alternatively, chimeric gene constructs may be produced in which the nucleotide regulatory sequences used to drive the expression of any of the nucleotide coding sequences that will yield any of the protein variants described supra may include but are not limited to: the entire, or any portion of the endogenous NF-L or NF-H promoters of the founder animal into which the human NF-L or NF-H gene construct is being introduced, or any other promoter sequences that drive neuron-enriched expression including, but not limited to such promoters as those described in Section 5.1, i.e., the NF-M, NSE, APP or Thy-1 promoters. Any functionally equivalent promoters or promoter/enhancer complexes may be used.

In order to produce the gene constructs used in the invention, the same recombinant DNA and cloning methods which are well known to those skilled in the art may be utilized as were discussed in Section 5.1. In this regard, appropriate NF-L or NF-M sequences may be generated from human NF-L or NF-H cDNA and/or genomic clones. These techniques include the use of restriction enzyme sites at relevant positions within the NF-L or NF-H sequences, and/or various methods of site directed mutagenesis. Appropriate NF-L or NF-H sequences may then be isolated, cloned, and used directly to produce transgenic animals. The sequences generated may also be used to engineer the chimeric gene constructs that utilize regulatory sequences other than the human NF-L or NF-H promoters, again using the techniques described in Section 5.1. These chimeric gene constructs would then also be used in the production of transgenic animals.

In an alternative embodiment of the invention, chimeric gene constructs which include entirely different genes may be utilized to create transgenic animals that can be crossbred with the human NF-L or NF-H transgenic animals of the invention in order to determine the effects of the expression of such genes on the progression of the neuropathologies that are a feature of the invention. Any of the genes discussed in Section 5.1 for use in conjunction with NF-M transgenic animals may be used here. For example, the effects of interactions between other neuro-specific IFs, such as peripherin, α-internexin, or nestin, with any of the human NF-L or NF-H proteins described supra may be assessed in the transgenic animal model systems. To this end, a chimeric gene composed of all or part of the coding sequence for any of these genes, controlled by a neuron-enriched promoter such as the NF-L, NF-M, or NF-H promoters, described supra, can be produced. Alternatively, any of the NF-M gene constructs described in Section 5.1 may be used. In addition, the effects of interactions between other known or potential neurofibrillary tangle components, such as APP, APP β/A4 fragment, or tau protein, with any of the human NF-L or NF-H proteins described supra may also be assessed in the transgenic animal model systems. To this end, a chimeric gene composed of all or part of the coding sequence for any of these genes or gene fragments, controlled by a neuron-enriched promoter such as the NF-L, NF-M, or NF-H promoters, described supra, may be produced. The use of such transgenes to produce transgenic animals will result in animals that express or overexpress, in a neural-specific manner, whichever of these coding sequences is present on the transgenic construct. The effects of such transgenic IF, β/A4, or tau protein expression on the progression of neurodegenerative pathologies can be assessed by crossbreeding such transgenic animals with any of the NF-L or NF-H transgenic animals.

In yet another embodiment of the invention, transgenic animals may be produced in which the function of one or more endogenous genes have been disrupted. These transgenic animals can then be crossbred with the human NF-L or NF-H transgenic animals of the invention in order to determine the effects that the lack of expression of such endogenous genes has on the progression of the neuropathologies that are a feature of the invention. Any of the genes discussed in Section 5.1 as targets for disruption in conjunction with NF-M animals may be used here. For example, the disruption of one or more of the endogenous neural-specific IFs such as NF-L, NF-M, NF-H, peripherin, α-internexin and nestin, the disruption of proteins that may modify human NFs, such as the neurofilament-specific protein kinase, or the disruption of endogenous genes encoding components of neurofibrillary tangles, such as tau proteins, may be assessed. To accomplish these endogenous gene disruptions, the technique of site-directed inactivation via gene targeting (Thomas, K. R. and Capecchi, M. R., 1987, Cell 51:503–512) as discussed in Section 5.1 may be used. The effects of such disruptions of endogenous gene function on the progression of neurodegenerative pathologies can be assessed by crossbreeding such transgenic animals with any of the NF-L or NF-H transgenic animals.

5.3 Production of Transgenic Animals

Animals of any species, including but not limited to mice, rats, rabbits, guinea pigs, pigs, micro-pigs, and non-human primates, e.g., baboons, squirrel monkeys and chimpanzees may be used to generate the transgenic animals of the invention. Any technique known in the art may be used to introduce the transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

Once the founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the neuropathological effects of expression. One such approach, which was used to develop the NF-M 27 line described in the examples, infra, is to cross the founder animals with a wild type strain to produce an F1 generation that exhibits neuropathological disorders, such as neurofibrillary tangles. The F1 generation may then be inbred in order to develop a homozygous line.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems.

5.4 Selection and Characterization of the Transgenic Animals

The transgenic animals that are produced in accordance with the procedures detailed in Sections 5.1 and 5.2 should be screened and evaluated to select those animals which may be used as suitable animal models for neurodegenerative disorders.

Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and reverse transcriptase-PCR (rt-PCR). Samples of brain may be evaluated immunocytochemically using antibodies specific for human NF-M, such as H014 (Lee, V. M. -Y et al., 1988, Proc. Natl. Acad. Sci. USA 85:1998–2002) and the like.

The NF transgenic animals that express NF mRNA or protein (detected immunocytochemically, using antibodies directed against NF and/or tag epitopes) at easily detectable levels should then be further evaluated histopathologically to identify those animals which display such neuropathologies as neurofibrillary tangles, axonal and/or cell body swelling, increased axonal caliber, slow axonal transport, dendritic and/or perikaryal neurofilament accumulations. Such transgenic animals serve as suitable model systems for neurodegenerative disorders.

5.5 Uses of the Transgenic Animals

The transgenic animals of the invention may be used as a model system for human neurodegenerative disorders and/or to generate neuronal cell lines that can be used as cell culture models for these disorders.

The transgenic animal model systems for neurodegenerative disorders may be used as a test substrate to identify drugs, pharmaceuticals, therapies and interventions which may be effective in treating such disorders. Therapeutic agents may be administered systemically or locally. Suitable routes may include oral, rectal, or intestinal administration; parenteral delivery, including intramuscular, subcutaneous, intramedullary injections, as well as intrathecal, direct intraventricular, intravenous, intraperitoneal, intranasal, or intraocular injections, just to name a few. The response of the animals to the treatment may be monitored by assessing the reversal of disorders associated with neurodegenerative disorders. With regard to intervention, any treatments which reverse any aspect of neuronal degeneration should be considered as candidates for therapeutic intervention. However, treatments or regimens which reverse the constellation of pathologies associated with any of these disorders may be preferred. Dosages of test agents may be determined by deriving dose-response curves.

The transgenic animal model systems for neurodegenerative disorders may also be used as test substrates in identifying environmental factors, drugs, pharmaceuticals, and chemicals which may exacerbate the progression of the neuropathologies that the transgenic animals exhibit. The example in Section 8 demonstrates this particular use.

In an alternate embodiment, the transgenic animals of the invention may be used to derive a cell line which may be used as a test substrate in culture, to identify both agents that reduce and agents that enhance the neuropathologies. While primary cultures derived from the transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

It is apparent that many modifications and variations of this invention as set forth here may be made without departing from the spirit and scope thereof. The specific embodiments described below are given by way of example only and the invention is limited only by the terms of the appended claims.

6. EXAMPLE: EXPRESSION OF HUMAN NF-M IN TRANSGENIC MICE

The creation and characterization of a line of transgenic mice which carry and express the gene encoding the midsize human neurofilament (NF-M) subunit is described in this working example. The transgenic animals contain a 8.5 kb DNA fragment bearing the coding sequence for human NF-M in addition to 2.8 kb of upstream sequence and approximately 500 bp of 3' non-coding sequence including the polyadenylation site.

It is shown that the human NF-M protein is found only in neurons and in no other cells of the transgenic mouse. Human NF-M was found in all regions of the CNS (central nervous system) and PNS (peripheral nervous system) tissue examined. The protein is fully phosphorylated and copolymerizes with the endogenous murine neurofilament proteins. While the level of human protein relative to that of endogenous NF-M protein is low, the human NF-M appears to be, in every way, a functional subunit within the murine neuron.

Different levels of human NF-M protein and mRNA were detected in different CNS regions. Since this difference in expression is seen at the mRNA as well as the protein level, it is most likely due to differences in the transcriptional efficiencies of the transgene or the stability of the mRNAs. This unexpected result is most dramatically illustrated in the hippocampus, where different populations of axons contain vastly different amounts of the human NF-M. This pattern indicates that some specific types of neurons, with unique functions, express the transgenes more efficiently than others. Unlike previous transgenic studies, using either cosmid DNA corresponding to human NF-L (Julien, J. -P. et al., 1987, Genes and Dev. 1:1085–1095) or a MSV (murine sarcoma virus) NF-L fusion gene construct (Monteiro, M. J. et al., 1990, J. Cell Biol. 111:1543–1557), where no correlation could be determined between the levels of mRNA and protein in the CNS, the results described here show a distinct correlation between the mRNA and protein levels of human NF-M.

6.1 Materials and Methods

6.1.1 Transgenic Mice

DNA used to generate transgenic mice was prepared from the plasmid pTZNF-M. (Pleasure, S. J., et al., 1990, J. Neurosci. 10:2428–2437). PTZNF-M was digested at the unique Kpn1 and BstX1 sites and an 8.5 kb fragment was isolated which contains the 3 exons and 2 introns of the human NF-M gene plus 2.8 kb of upstream sequence and 500 bp of 3' non-coding sequence including the polyadenylation site. DNA was purified from agarose by 2 rounds of Geneclean (Bio 101). The DNA was eluted in microinjection buffer (10 mM Tris-HCl pH 7.4, 0.2 mM EDTA) and then filtered twice through 0.2 μm filters. DNA concentration was estimated by ethidium bromide staining and diluted to 5 ng/μl.

Transgenic mice were produced in the Mount Sinai School of Medicine Transgenic Core Facility. Microinjection and manipulation procedures were as described by Hogan et al. ("Manipulating the Mouse Embryo," 1986, Cold Spring Harbor Laboratory, Cold Spring Harbor, N.Y.) with only minor modifications. C57B1/6J×DBA/2J $F_1$ hybrids were used as the source of fertilized eggs and were re-implanted into CD-1 pseudopregnant females. Transgenic founders were identified by Southern blotting of genomic DNA isolated from tail tissue. Blots were screened with a $^{32}$P-labeled probe specific for the human NF-M gene made with a random primer kit (Promega) utilizing the 630 bp Bgl2/EcoR1 fragment of the second intron of human NF-M. The founder was mated with B6D2 $F_1$ females and additional transgenic progeny were identified either by Southern blotting or by polymerase chain reaction. Transgene copy number was estimated from slot blots containing 10 μg of genomic DNA and a series of DNA standards which were hybridized with the same probe as was used for Southern blotting. Copy number was estimated by densitometry.

6.1.2 RNA Analysis

Adult mice were sacrificed by cervical dislocation. Total cellular RNA from a variety of neural and non-neural tissues was isolated with guanidinium thiocyanate based on the method of Chirgwin et al. (Chirgwin, J. M., et al., 1979, Biochemistry 18:5294–5299). Tissues were homogenized in 4M guanidinium thiocyanate with a tissumizer (Tekmar, Cincinnati, Ohio) and the RNA was pelleted through step gradients of 2.4M and 5.7M CsCl in an SW41 rotor at 30,000 RPM for 24 hrs. The RNA pellets were solubilized in 10 mM tris-HCl (pH 7.5), 1 mM EDTA, 5% sodium lauryl sarcosine and 5% phenol and were then extracted with phenol/chloroform before being precipitated twice with sodium acetate and ethanol.

RNAase protection assays were performed essentially as described by Ausubel et al. (Ausubel, F., et al., 1987, Current Protocols in Molecular Biology, John Wiley & Sons, New York). Uniformly labeled RNA probes were synthesized with T3 or T7 RNA polymerase and 100 μCi of ($\alpha$-$^{32}$p) UTP. To construct a probe template for the human NF-M transgene, the 727 bp BamH1 fragment from exon 3 of human NF-M was cloned into BamH1 site of Bluescript SK11 (pBS, Stratagene). This plasmid was digested with Sty1 and Xba1 which eliminates all the NF-M sequence except for the BamH1-Sty1 fragment (nucleotides 1656–1792 (Myers, M. W., et al., 1987, EMBO J. 6:1617–1626)). The Xba1 and Sty1 sites were filled in with the Klenow fragment of DNA polymerase I and relegated and subcloned. Probes were synthesized with T3 RNA polymerase after linearizing the plasmid with EcoR1. This probe protects a 129 bp fragment of Human NF-M. For murine NF-M doublestranded synthetic oligodeoxynucleotides with BamH1 and EcoR1 cohesive ends containing mouse NF-M sequence from exon 3 (nucleotides 4490–4554 (Levy, E. et al., 1987, Eur. J. Biochem. 166:71–77)) were subcloned into EcoR1/BamH1 digested pBS. Probes were synthesized with T7 RNA polymerase after linearizing the plasmid with Xba1. This probe protects a 65 bp fragment of mouse NF-M. A probe template for murine β-actin sequence (nucleotides 79–151 (Tokunaga, K., et al., 1986, Nucl. Acids Res. 14:2828) was subcloned into pBS in a manner similar to the murine NF-M template. This probe protects a 73 bp fragment of murine β-actin. After overnight hybridization at 45° C. samples were digested with RNAase A (80 μg/ml, Sigma) and RNAase T1 (700 units/ml, Boehringer-Mannheim) and then processed as described by Ausubel et al. (Ausubel, F., et al., 1987, Current Protocols in Molecular Biology, John Wiley & Sons, New York) except that 150 μl of 7.5M ammonium acetate was added before the final ethanol precipitation. Protected fragments were localized by autoradiography and quantitated by densitometry.

6.1.3 Monoclonal Antibodies

The monoclonal antibodies (MAbs) selected for this study have been described previously. In Lee, V. M. -Y., et al., 1987, J Neurosci. 7:3474–3488; Lee, V. M. -Y., et al., 1988, Proc. Natl. Acad. Sci., USA, 85:1998–2002; (Pleasure, S. J., et al., 1990, J. Neurosci. 10:2428–2437). Briefly, H014 is a MAb which was raised in rat using human NF-M as immunogen. This MAb binds specifically to the highly phosphorylated forms of the multiphosphorylation repeat domain in human NF-M and does not recognize mouse NF-M. In contrast, RM0108 and RM0291 are mouse MAbs which were raised to rat NF-M and recognize an epitope in the COOH tail domain of mouse NF-M, but not human NF-M. Both RM0254 and RM0292 bind to mouse and human NF-M although with different affinities (see below). Finally, RM0255 which recognizes a phosphate independent epitope in the last 20 amino acids of both mouse and human NF-M polypeptides binds equally well to mouse and human NF-M (Balin, B. J., et al., 1991, Brain Res. 556:181–195).

6.1.4 Indirect Immunofluorescence and Immunoelectron Microscopy

Control and transgenic mice were perfused with buffered 4% paraformaldehyde, and the brains and spinal cords were removed, frozen, and sectioned by crytostat at 6–10 μm thickness. Immunofluorescence staining for endogenous and transgenic NF-M proteins was performed separately or simultaneously using monoclonal antibodies listed above, visualized with species-specific fluoresceinated or biotinylated secondary antibodies (Amersham) and fluorescein- or rhodamine-labeled streptavidin. Sections were counterstained with the blue-emitting fluorescent dye 4', 6-diamidino-2-phenylindode hydrochloride (DAPI).

Immunoelectron microscopy was conducted on enriched NF preparations isolated from mouse nerve roots. Briefly, nerve roots from 4 mice were carefully dissected and an enriched cytoskeletal preparation was prepared as previously described (Balin, B. J., et al., 1991, Brain Res. 556:181–195). NFs were absorbed on carbon, formvar-coated grids and processed for immunoelectron-microscopy as described. Since double immunolabeling experiments were conducted, the primary antibody incubations were performed simultaneously using H014 (rat immunoglobulin) and RM0291 (mouse immunoglobulin). Subsequently, goat antisera to rat and rabbit antisera to mouse that were conjugated to 10 and 5 nm gold particles respectively were used to detect the primary MAbs.

6.1.5 Preparation of Brian Samples for Quantitative Western Blotting

Six regions of brains from both transgenic and wild type mice were dissected carefully and weighed. These 6 regions included: hippocampus, neocortex, cerebellum, brain white matter, hypothalamus and spinal cord. One ml of hot I X Sample Buffer (10% sucrose, 10 mM Tris pH6.8, 1 mM EDTA, 40 mM DTT, 1% SDS) per 100 mg of wet tissue was used to homogenize these regions. Samples were then boiled for 5–10 mins, transferred to microfuge tubes and spun at 150,000×g in a Beckman TL100 for 30 mins at 25° C. to pellet insoluble material. The supernatant was then transferred to new tubes and the protein concentration in each sample was determined using the Pierce Bradford Kit and bovine serum albumin as standards. Samples were then diluted to give a uniform concentration (i.e. 3 mg/ml) using 5X sample buffer with dye. Other regions of the CNS and PNS as well as non-neural tissue were also analyzed qualitatively using the peroxidase antiperoxidase method as described (Lee, V. M. -Y., et al., 1987, J. Neurosci. 7:3474–3488; Lee, V. M. -Y., et al., 1988, Proc. Natl. Acad. Sci., USA, 85:1998–2002).

6.1.6 Purification of Mouse and Human NF-M Standards

Crude NF preparations from mouse and human spinal cords were prepared as previously described (Carden, M. J., et al., 1985, J. Biol. Chem. 260:9805–9817). Because of the limited number of spinal cords that are available from mouse and human for NF isolation and because of the inability to enrich for NF proteins by dissecting out the gray matter from the spinal cords, it was difficult to recover sufficient amount of purified NF-M using the conventional HPLC purification protocol as described previously (Balin, B. J., et al., 1991, Brain Res. 556:181–195). However, highly purified mouse and human NF-M was recovered in sufficient quantities by separating enriched NF preparations on SDS-PAGE gels and electro-elution of the NF-M protein bands. Since human NF-M but not mouse NF-M exhibited some breakdown products after electro-elution, we determined the exact amount of full length NF-M contained within a known amount of our human NF-M preparation by SDS-PAGE gels, followed by densitometry. From the densitometry scan, we determined the percentage of the amount loaded which existed as intact full length NF-M.

6.1.7 Gel Electrophoresis and Quantitation

Protein samples were analyzed by the electrophoretic procedure of Laemmli (Laemmli, U. K., 1970, Nature 227:680–682) using 4–8% gradient or straight gels and transferred to 0.45 μm nitrocellulose as previously described (Balin, B. J., et al., 1991, Brain Res. 556:181–195). The nitrocellulose was treated for quantitative immunoblotting by the procedure described by Earnshaw (Earnshaw, W. C., et al., 1987, J. Cell Biol. 104:817–823) using the MAbs described above. Labeled bands were visualized using $^{125}$I-labeled goat anti-mouse IgG (NEN) as the secondary antibody. Quantitation of the radiolabelled bands was conducted as previously described (Clark, E. A. et al., 1991, Lab. Invest. 64:35–44).

6.2 Results

6.2.1 Tissue Distribution of Human NF-M mRNA In Transgenic Mice

The NF-M gene excised from pTZNF-M was purified and used to create transgenic mice. Three founder transgenic mice were identified among 27 pups. One, a male, passed the trait on to progeny and established a NF-M transgenic mouse line (designated as NF-M 27). The others, both females, either died before weaning, or did not pass on the trait. Southern blot analysis revealed that the NF-M 27 line contained 5 copies of the transgene. The studies described here utilized NF-M 27 heterozygous transgenic mice and their control littermates.

The expression of human NF-M mRNA was analyzed in brain and in a variety of non-neural tissue using the RNAase protection assay. High levels of human NF-M mRNA were found in transgenic mouse brain, while very low levels of transgene mRNA were detected in non-neural tissues (FIG. 1A). Of the non-neural organs tested, spleen and intestine showed the highest levels (about 7–10% of brain) of human NF-M mRNA expression as estimated by densitometry. However, with long film exposures of the RNAase protection assays, most non-neural tissues were found to contain a very low level of NF-M mRNA. This may be due to the presence of enteric ganglia in the intestine and of nerve fibers in other organs, but, it could also indicate the absence of important genetic elements in the transgene, or a position effect due to the insertion site of the transgene. Nevertheless, human NF-M mRNA in the transgenic mice was expressed at a level at least 10 to 100 fold higher in brain than in any of the non-neural tissues examined here (FIG. 1A).

Next, the relative level of transgene to endogenous NF-M mRNA in brain and spinal cord of transgenic mice using the RNAase protection assay was compared. As shown in FIG. 1B, the ratio of transgenic to endogenous NF-M is much higher in the brain (25%+/−3.4) than in spinal cord (3.3%+/−2.3) indicating regional differences exist in the expression of the transgene.

6.2.2 Immunocytochemical Localization of Human and Mouse NF-M in Transgenic Mice To determine whether human NF-M protein is expressed only in neurons, indirect immunofluorescence was performed on tissue sections of spinal cord from control and transgenic mice using a rat MAb that is specific only for human NF-M (HO14) or a mouse MAb that is specific only for mouse NF-M (RMO108). Sections from transgenic mouse brain showed strong immunoreactivity for human NF-M, while comparable sections from non-transgenic control mice were completely negative (compare FIG. 2A with FIG. 2C). Human NF-M staining was limited to axons; no immunoreactivity in glial or endothelial cells was seen. Neuronal perikarya were not stained in the preparations because the MAb used recognizes a highly phosphorylated epitope within the multiphosphorylation repeat domain of NF-M, and this phosphorylated epitope is normally found only in axons (Tohyama, T. et al., 1991, J Comp. Neurol. 310:285–299). In longitudinal sections cut from spinal cord, individual axons bearing the human NF-M protein could often be followed over substantial distances (FIG. 3A). Double-labeling experiments using species-specific MAbs showed that the endogenous mouse and transgenic human NF-M proteins are present together in individual axons of the transgenic mice (compare FIG. 3A with 3B). These data demonstrate that, within the sensitivity of the immunocytochemical technique, the human NF-M protein is present only in neurons in the central nervous system and is most frequently present in the same axons as endogenous mouse NF-M.

6.2.3 Immuno-Electron Microscopic Localization of Human and Mouse NF-M Isolated NFS In order to assess whether or not human and endogenous NF-M proteins co-assemble into the same filament, enriched NF preparations isolated from nerve roots of transgenic mice were absorbed onto formvar coated grids and immunolabeled with HO14 (human specific) and RMO108 (mouse specific) anti-NF-M MAbs. Using secondary antibodies specific for the rat MAb, i.e. HO14 (10 nm gold particles) and for mouse MAb, i.e. RMO108 (5 nm gold particles), it is evident that the 10 nm diameter NFs are decorated by both 5 and 10 nm gold particles, demonstrating that human and mouse NF-M proteins are present in the same filament. (FIGS. 4A–4B).

6.2.4 Relative Abundances of Endogenous and Transgenic NF-M in Transgenic Mice

In order to assess the levels of human NF-M protein expression in different brain regions of the transgenic mice, the relative levels of human NF-M protein expression with that of endogenous mouse NF-M in the same brain regions were compared. Since human NF-M on SDS-PAGE gels has an Mr of 170 kD and mouse NF-M has an Mr of 145 kD (Lee, V. M. -Y. et al., 1986, J. Neurosci. 6:2179–2186), they can be resolved easily on a 4–8% gradient SDS-PAGE gel. Using a MAb (RMO254) which recognizes human NF-M better than mouse NF-M, it is evident that the distribution of human NF-M in different regions of the brain differs from those of the endogenous mouse NF-M (FIGS. 5A and 6A–6B). Because the level of human NF-M expression is quite low when compared to that of endogenous mouse NF-M, it is essential that RMO254, with its higher affinity for human NF-M, be used in this study (FIG. 5 and see below). The differential expression of the endogenous and transgene NF-M is best revealed by comparing the ratio of the two NF-M proteins in the same brain region. Using known quantities of human and mouse NF-M as standards, we showed that the expression of human NF-M was generally low when compared to that of endogenous mouse NF-M (FIGS. 5 and 7). The highest level of human NF-M expression was found in hippocampus where the amount of human NF-M expressed is approximately 25% that of endogenous NF-M. The lowest level of human NF-M expression is found in spinal cord, where the human NF-M levels are only 3% that of the endogenous NF-M spinal cord expression. Sciatic nerve and dorsal root ganglia appear to have a similar ratio (0.03) of transgene to endogenous NF-M (data not shown).

Finally, the levels of endogenous NF-M in transgenic mice versus wild type littermates were compared. The results suggest that, despite a 25% increase in total NF-M (due to the human NF-M expression) in the hippocampus, the endogenous NF-M in the transgenic mice remained the same as in the wild type (FIG. 8). Thus, expression of the human NF-M gene and the presence of human NF-M protein does not appear to alter the expression of the endogenous mouse NF-M gene.

To further characterize regional differences in transgene expression, cryostat sections of brain for transgenic and endogenous NF-M proteins were stained by simultaneous two-color immunofluorescence, using species-specific primary and secondary antibodies. Staining for the endogenous mouse protein was found in all brain regions and appeared identical in control and transgenic specimens. Immunoreactivity for human NF-M was also widely distributed. In cerebral cortex and in most other areas of the brain, axons exhibiting staining for human NF-M also usually stained for murine NF-M; however, many axons which contained the endogenous protein showed no detectable signal for the transgenic protein.

The hippocampal formation was striking (FIGS. 10A–10C). Both control and transgenic mice showed marked staining for the endogenous NF-M protein in the hilus of the dentate gyrus, within a prominent band immediately superficial to the pyramidal cell layer (2 in FIG. 10A), and in a minor band immediately deep to it. This distribution appears identical to that of mossy fibers. This endogenous NF-M staining appeared the same in control and transgenic mice, both in distribution and in intensity. The transgenic mice additionally showed very strong immunofluorescence staining for the human NF-M protein, in a band distinct from, and superficial to, that containing the endogenous murine NF-M (1 in FIG. 10C) and in a second band deep to the pyramidal cell layer (3,4 in FIG. 10C). The fornix also showed segregation of murine and human NF-M: the dorsal most portion stained strongly for murine, but weakly for human NF-M, while the ventral most part showed the reverse pattern (not illustrated).

These results are consistent with those from quantitative immunoblotting, which showed the transgenic brain to have higher levels of human NF-M protein in the hippocampus than in other brain regions (FIGS. 6A–6B), and to have normal levels of the endogenous murine NF-M protein in the same region (FIG. 8). In contrast to the pattern predominant in cerebral cortex, in other brain regions, as well as in the spinal cord, the transgenic and native NF-Ms of the hippocampus are contained in different axon populations.

7. EXAMPLE: TRANSGENIC MURINE MODEL FOR NEURODEGENERATIVE DISEASES

Described here is the characterization of transgenic mice that exhibit brain neurofibrillary accumulations, including tangles as they age, while their nontransgenic littermates do not, and furthermore, exhibit a marked sensitivity to aluminum, an environmental agent thought to play a role in some neurodegenerative processes. Such transgenic mice are as the transgenic line discussed in the working example in Section 6, supra, i.e. the mice carry and express the human NF-M gene.

The transgenic animals described here can serve as an economical research tool for probing the origins, prevention, or amelioration of neurofibrillary tangle formation. These animals can also be useful in toxicological investigations designed to identify and evaluate environmental agents which exacerbate tangle formation.

7.1 Materials and Methods

7.1.1 Transgenic Mice

All methods used here, which involve the production and characterization of transgenic lines of mice, are as described in Section 6.1.

7.1.2 Histological Identification and Enumeration of Neurofibrillary Accumulations Mice were perfused with buffered 4% paraformaldehyde and their brains removed, and either frozen or paraffin imbedded and sectioned. For fluorescent visualization, the sections were treated as described in Section 6.1.4. Sections were stained with Bielschowsky silver impregnation stains and/or hematoxylin and eosin as in Kowall, N. W., et al. Neuroscience 29:329–337 (1989) and Sheenan, D. C. and Hrapchak, B. B., *Theory and Practice Histotechnology*, Second Edition 1980 Battelle Press, Columbus. Coronal sections were manually scanned under light microscopy for silver stained neurofilament accumulations. Two types of neurofilament pathological structures were identified and scored separately in silver-stained specimens: the perinuclear, spherical accumulations (Pick-like-bodies) and the perinuclear elongated accumulations (neurofibrillary accumulations or tangles). When comparing brains of aluminum treated and wild type or untreated mice equal numbers of anatomically comparable whole coronal sections were manually scanned and scored for neuropathology.

7.1.3 Aluminum Treatment

Transgenic and wild type mice were treated with aluminum by a single intercerebral injection of 1 µl of unbuffered 1 mM $AlCl_3$ solution. The injection site was just lateral to the ventricle or the ventricle itself. Injections were performed with the aide of stereotactic guidance. The neuropathological disease was allowed to develop for two weeks before the animals were sacrificed and their brain tissues examined histologically by the methods described above.

7.2 Results

7.2.1 Neurofibrillary Tangle Formation in Aged Animals

Transgenic mice carrying an 8.5 kb fragment of genomic DNA containing the human NF-M coding sequence plus 2.5 kb of upstream sequence and approximately 500 bp of 3' untranslated sequence have previously been characterized (see Section 6). These transgenic mice express the human NF-M protein in a neural-specific fashion. The protein is fully phosphorylated, and copolymerizes with the endogenous neurofilament proteins. Immunostained material of CNS tissue obtained from mice 3 months old and younger, showed no indication that the transgenic mice had developed axonal spheroids, neurofilamentous accumulations or other pathological changes. Thus, the human NF-M protein appeared to be, in every way, acting as a functional, nondeleterious subunit in the transgenic mice studied.

As is standard practice, all of the animals in our previous study were characterized by the age of 3 months. In this study, however, we find that if transgenic mice derived from the same line as the previous study are allowed to age before neuropathological examination, a substantially different result is obtained. As is shown in FIG. 11, neurofibrillary pathologies, including tangles accumulate in the brains of the transgenic mice as they age. No neurofibrillary accumulations can be detected in the brains of the nontransgenic littermates (data not shown). The tissues shown in FIG. 11 are from a 4.6 month and a 27 month old mouse and exhibit several neuropathologies in a single high magnification microscope field. Neurofibrillary accumulations are detectable in mice as young as 4.6 months old, but are more abundant in older mice.

7.2.2 Aluminum Treatment of Transgenic and Wild Type Animals

In addition to neurofibrillary tangle accumulation as they age, the human NF-M transgenic mice exhibit at least one other distinct difference relative to their nontransgenic littermates. Namely, the transgenic mice are markedly more sensitive to certain environmental agents, such as aluminum, that are thought to play a role in the progress of certain neurodegenerative processes.

In this study, both transgenic and nontransgenic (wild type) littermates were given intracerebral inoculations of solutions of aluminum chloride. In FIG. 12 is shown the results of one such study. Here, 3 month old wild type (wt) and transgenic (NF-(NF-M 27) mice were administered aluminum chloride and examined as described Sections 7.1.2 and 7.1.3. The transgenic mice, in contrast to wild type mice, exhibited neuropathologies that were large, numerous, and prototypical. Pick-like bodies and tangles were observed that extended from the nucleus to far down the axon. Note, however, that because there is variability in the intensity of silver staining, particularly with Bielschowsky silver impregnation stain, and because silver staining illuminates several structures, like the nucleoli, in addition to neurofilaments, great care must be exercised in identifying neurofilament pathologies. In our experiments we scored only neurofibrillary accumulations that were perinuclear.

FIG. 13 reports the results of a "blinded" neuropathological examination of several sections from four transgenic and two wild type three month old mice that had been treated by a single inter-cerebral injection of 1 mM aluminum chloride solution. Brain tissue was examined for the presence of neurofibrillary tangles and Pick-like bodies (spherical aggregates of abnormal filaments). As the table in FIG. 13 shows, few, if any, of these abnormal structures appeared in the brains of the wild type animals, but extensive tangles and Pick-like bodies are detectable in each of the transgenic mice. The low level of tangles and pick-like bodies reported for aluminum treated wild type mice are at the threshold of accuracy for the methods used, and although reported in this blinded experiment, they probably are not true neuropathologies.

8. EXAMPLE: TRANSGENIC MICE CARRYING ALTERED VERSIONS OF THE HUMAN NF-M GENE

In Sections 6 and 7, it was demonstrated, first, that an 8.5 kb fragment of genomic DNA containing the human NF-M coding sequence plus 2.5 kb of upstream sequence and approximately 500 bp of 3' untranslated sequence was sufficient to drive neuron-enriched expression of human NF-M in transgenic mice, and further, that the presence of human NF-M in aging mice caused the appearance of neurofibrillary tangles that are a hallmark of many human neurodegenerative diseases. In addition, human NF-M causes even young mice to exhibit an increased sensitivity to certain environmental factors, such as aluminum, that may play a role in the progression of some neurodegenerative disorders.

In the example described below, the role of the human NF-M protein in the development of these neuropathological phenomena is examined by producing transgenic mice carrying truncated versions of the human NF-M protein. Specifically, the production of transgenic mice engineered with truncated genes encoding human NF-M subunits that are deleted for portions of either the amino terminus, the carboxy terminus, or the KSP domains are described.

8.1 Materials and Methods

8.1.1 Preparation of a Gene Encoding a "Tagged" NF-M Subunit and Its Deletions A modification of a polymerase chain reaction (PCR) procedure independently developed by M. Schubert (unpublished experiment) and Kamman et al. (Kamman et al., 1989, Nucl. Acids Res. 17:5404) is employed for the preparation of both the gene encoding the tagged NF-M protein and the tagged alterations of the protein. Briefly, the procedure uses three sequence specific oligonucleotide primers for the synthesis of the amplified DNA. Two of the primers correspond to the termini of the desired product while the third contains the sequence to be inserted flanked by sequences complementary to the template at the desired site of insertion (FIGS. 14A, B, C). In cases where deletions are desired, the third primer consists of sequences flanking the desired deletion. The portions of the human NF-M gene with the primer sequences are diagrammed in FIGS. 14A–14C. Primer 1 is a 73 mer containing the 33 nucleotides that encode the 11 amino acid "tag". Primers 2 and 3 correspond to sequences outside the Sma-1 Xho-1 fragment, so that the PCR product will extend beyond these sites and can be restricted with these enzymes, yielding precise termini.

In FIG. 14A, the syntheses initiated with primers 1 and 3 yield transcripts a and b. Primer 2 can initiate synthesis on these transcripts to yield products c and d. Product c can act as a primer itself and thus can be further elongated to produce product e. The primers are complementary to the termini of products c, d, and e, and these products are amplified in subsequent rounds of syntheses. The PCR product is cleaved at the Sma-1 and Xho-1 sites and purified by electrophoresis. This DNA fragment is inserted into a plasmid bearing an NF-M gene that has been restricted with Sma-1 and Xho-1. The resulting gene encodes NF-M protein bearing a tag near the N-terminus and is referred to as the N-terminally tagged protein. A second differently tagged NF-M gene is prepared by inserting a short, synthetically synthesized double stranded DNA into the Hind III site that lies near the beginning of the region and encoding the glutamate-rich region. This insertion preserves the reading frame, recreates a single Hind III site and produces a gene encoding an NF-M protein bearing a tag near the glutamate-rich domain termed C-terminal tagged protein.

Deletions are created in tagged NF-M genes by essentially the same PCR method used to make the tagged gene. In the case of the Glu-rich domain (FIG. 14C), the desired deletion site is sufficiently close the Hind-III site that the primer includes the restriction site and, thus, only two primers are necessary to generate a useful PCR product. The PCR products are cleaved with restriction enzymes (Xma-3, in the case of the amino terminal domain deletion, Hind-III, in the case of the deletion of the Glu-rich or carboxy terminal domains, BamH1, in the case of the deletion of the KSP repeat domain). Each of the restriction enzymes cleaves the pNF-M plasmid (into which the wild type human NF-M has been subcloned) only twice, at the indicated positions, thus allowing a simple means of replacing the normal sequence with the PCR product.

8.1.2 Creation of Transgenic Mice

Transgenic mice are produced using the constructs made according to Section 8.1.1, in conjunction with the techniques described in Section 6.1.1.

8.1.3 Characterization of the Transgenic Mice

The transgenic mice of this study are characterized using the techniques described in Sections 6.1 and 7.1. However, because of the tag sequence, the protein encoded by the transgene can be identified and studied using monoclonal antibodies which we have prepared that specifically recognize the tag.

8.2 Results

Transgenic mice carrying "tagged" altered versions of the human NF-M gene are produced here, in order to further study the role of the human NF-M domains, especially in relation to each domain's possible role in the appearance of the neuropathological phenotypes seen when intact human NF-M genes are introduced into mice.

8.2.1 Human NF-M Transgene Contructs

Gene constructs that produce truncated, "tagged", versions of the human NF-M protein are constructed for use in creating transgenic mice. The "tag" is an 11 amino acid peptide (see FIG. 14A) that is present at the amino or the carboxy terminus of each of the truncated NF-M proteins. It is not normally a part of the NF-M protein, but can be used to immunocytochemically identify the altered NF-M product irrespective of the regions deleted. Monoclonal antibodies of exceptional titers have already been produced against this "tag" sequence.

The truncated NF-M proteins produced have deletions of either the amino terminal (head) domain, KSP domain, or the carboxy terminal (tail) domain. Specifically, the amino terminal truncation deletes from amino acid 23 to amino acid 80; the KSP truncation deletes from amino acid 613 to 690; and the carboxy terminal truncation deletes from amino acid 795 to amino acid 914.

Additionally, a truncated human NF-M gene construct is designed that encodes a protein deleted for the KSP domain and part of each of the flanking domains (i.e., the Glu-rich and carboxy terminal domains). To produce this gene construct, the approximately 750 base pairs of sequence that lie between the two Bam H1 sites in the coding region of interest (see FIG. 14C) are deleted. This accomplished by Bam H1 digestion of a plasmid bearing the gene and subsequent religation.

9. EXAMPLE: PRODUCTION OF DNA CONSTRUCTS THAT CONTAIN ALTERED VERSIONS OF THE HUMAN NF-M GENE

In the example described below, a human NF-M gene construct that can be used as a transgene which will provide further information concerning the role of the human NF-M gene in the development of neuropathologies. Specifically, a truncated human NF-M gene that encodes a protein deleted for the glutamate-rich (Glu-rich) domain is produced. This Glu-rich domain truncation deletes the region from amino acid 451 to amino acid 611.

10. DEPOSIT OF EMBRYOS

The following mouse (MUS musculus) embryo strain carrying the listed plasmid has been deposited with the American Type Culture Collection (ATTC), Rockville, Md., and has been assigned the following accession number:

| Host Embryo | Strain | Plasmid | Deposit Date | Accession No. |
| --- | --- | --- | --- | --- |
| Mouse (Mus musculus) | NF(M)27 | pTZNF-M | Jan 20, 1993 | 72012 |

The following listed *E. coli* strain was deposited with the ATCC on Feb. 24, 1995, and has been assigned the following accession number:

| Strain | Accession No. |
|---|---|
| *E. coli* HB101, containing plasmid pTZNF(M) | 69752 |

The present invention is not to be limited in scope by the embryo deposited since the deposited embodiment is intended as illustration of an individual aspect of the invention and any embryos or constructs which are functionally equivalent are within the scope of this invention. Indeed various modifications of the invention in addition to those shown and described herein will become apparent to those skilled in the art from the foregoing description and accompanying drawings. Such modifications are intended to fall within the scope of the appended claims.

What is claimed is:

1. A transgenic mouse which exhibits brain neurofibrillary tangles and Pick-like bodies, containing, integrated into its genome, a transgene, comprising a human neurofilament subunit M (NF-M) coding sequence controlled by a human neurofilament subunit M (NF-M) regulatory sequence which drives neural-enriched expression of the human neurofilament subunit M (NF-M) coding sequence in the transgenic mouse, wherein the transgenic mouse is an embryo deposited with the American Type Culture Collection, having an accession number 72012 or progeny thereof.

2. A transgenic mouse or progeny thereof, containing, integrated into its genome, a transgene comprising the human neurofilament subunit M (NF-M) coding sequence controlled by the human neurofilament subunit M (NF-M) regulatory sequence, which drives neural-enriched expression of the human neurofilament subunit M (NF-M) coding sequence in the transgenic mouse so that the mouse exhibits brain neurofibrillary tangles and Pick-like bodies.

3. The transgenic mouse of claim 2, wherein the human neurofilament subunit M (NF-M) coding sequence and regulatory sequence are obtained from plasmid pTZNF-M, deposited with the American Type Culture Collection, within the *E. coli* strain HB101 having an accession number 69752.

* * * * *